US012797437B2

(12) United States Patent
Sun et al.

(10) Patent No.: US 12,797,437 B2
(45) Date of Patent: Nov. 17, 2026

(54) PEPTIDE INHIBITORS OF BETA-LACTAMASE AGAINST ANTIBIOTIC RESISTANCE

(71) Applicant: The Curators of the University of Missouri, Columbia, MO (US)

(72) Inventors: Hongmin Sun, Columbia, MO (US); Xiaoqin Zou, Columbia, MO (US); Xiao Heng, Columbia, MO (US); Xianjin Xu, Columbia, MO (US); Juan Ji, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 981 days.

(21) Appl. No.: 17/999,974

(22) PCT Filed: Jun. 4, 2021

(86) PCT No.: PCT/US2021/035849
§ 371 (c)(1),
(2) Date: Nov. 28, 2022

(87) PCT Pub. No.: WO2021/247965
PCT Pub. Date: Dec. 9, 2021

(65) Prior Publication Data

US 2023/0218707 A1 Jul. 13, 2023

Related U.S. Application Data

(60) Provisional application No. 63/034,528, filed on Jun. 4, 2020.

(51) Int. Cl.
*A61K 38/08* (2019.01)
*A61K 31/43* (2006.01)
*A61K 31/546* (2006.01)
*A61P 31/04* (2006.01)

(52) U.S. Cl.
CPC .............. *A61K 38/08* (2013.01); *A61K 31/43* (2013.01); *A61K 31/546* (2013.01); *A61P 31/04* (2018.01)

(58) Field of Classification Search
None
See application file for complete search history.

(56) References Cited

U.S. PATENT DOCUMENTS 5,912,231 A * 6/1999 Houghten .............. C07K 14/46 514/3.3
2004/0123343 A1 6/2004 La Rose et al.
2005/0186197 A1 8/2005 Palzkill et al.
2008/0213430 A1 9/2008 Segura et al.
2020/0165309 A1 5/2020 Yount et al.

OTHER PUBLICATIONS

Bush K and Bradford P "Beta-Lactams and Beta-Lactamase Inhibitors: An Overview" Cold Spring Harbor Perspectives in Medicine 6:a025247. (Year: 2016).*
Silva et al. "Beta-Lactamase inhibitor peptides as the new strategies to overcome bacterial resistance" Drugs of Today 54:737-746. (Year: 2018).*
Jiravanichpaisal et al. "Antibacterial peptides in hemocytes and hematopoietic tissue from freshwater crayfish *Pacifastacus leniusculus*: Characterization and expression pattern" Developmental and Comparative Immunology 31:441-455. (Year: 2007).*
GenBank ABP88042.1 (Year: 2007).*
Bruno et al., Basics and recent advances in peptide and protein drug delivery; Ther. Deliv., 2013, vol. 4, No. 11, pp. 1443-1467.
CDC: Antibiotic Resistance Threats In The United States, 2019. U.S. Department of Health and Human Services, Centers for Disease Control and Prevention. 88-pages.
Clinical and Laboratory Standards Institute, Advancing Quality in Health Care Testing; M07-A9, vol. 32, No. 2, Replaces M07-08, vol. 29, No. 2, Jan. 2012, 88-pages.
Cockerill et al., Methods for Dilution Antimicrobial Susceptibility Tests for Bacteria that Grow Aerobically; Approved Standard—Ninth Edition; vol. 32, No. 2, replaces M07-A8; vol. 29, No. 2, Jan. 2012, pp. 1-88.
Docquier et al., An update of Beta-lactamase inhibitor discovery and development. Drug Resistance Updates, 36, 13-29 (Epub. Nov. 17, 2017).
Hofer U., The cost of antimicrobial resistance, Nature Reviews, Microbiology; 2019, vol. 17, No. 1, pp. 3.
Huang et al., A broad-spectrum peptide inhibitor of Beta-lactamase identified using phage display and peptide arrays; Protein Engineering, 2003, vol. 16, No. 11, pp. 853-860.
Jitendra et al., Noninvasive Routes of Proteins and Peptides Drug Delivery; Indian Journal of Pharmaceutical Sciences; Jul.-Aug. 2011, pp. 367-375.
Lau et al., Therapeutic peptides: Historical perspectives, current development trends, and future directions; Bioorganic & Medicinal Chemistry, 2018, vol. 26, pp. 2700-2707.
Lee et al., Conjugation of Cell-Penetrating Peptides to Antimicrobial Peptides Enhances Antibacterial Activity; ACS Omega, 2019, vol. 4, pp. 15694-15701.
Lowy, Antimicrobial resistance: the example of *Staphylococcus aureus*; Science in Medicine, J. Clin. Invest., 2003, vol. 111, pp. 1265-1273.
Merrifield et al., Solid phase peptide synthesis. I. The synthesis of a tetrapeptide. Journal of the American Chemical Society, 1963, vol. 85, pp. 2149-2154.

(Continued)

*Primary Examiner* — Sudhakar Katakam
*Assistant Examiner* — Zachary J Miknis
(74) *Attorney, Agent, or Firm* — Brownstein Hyatt Farber Schreck, LLP

(57) ABSTRACT

Disclosed herein are new peptide inhibitors against beta-lactam resistance that can improve the efficacy of currently available antibiotics. Methods of using the peptide inhibitors for treating bacterial infections are also disclosed.

10 Claims, 7 Drawing Sheets

Specification includes a Sequence Listing.

(56) References Cited

OTHER PUBLICATIONS

Oikawa et al., Screening of a Cell-Penetrating Peptide Library in *Escherichia coli*: Relationship between Cell Penetration Efficiency and Cytotoxicity; ACS Omega, 2018, vol. 3, pp. 1648916499.
Perez-Peinado et al., Mechanisms of bacterial membrane permeabilization by crotalicidin (Ctn) and its fragment Ctn(15-34), antimicrobial peptides from rattlesnake venom; JBC Article; J. Biol. Chem, 2018, vol. 293, No. 5, pp. 1536-1549.
Pinho et al., An acquired and a native penicillin-binding protein cooperate in building the cell wall of drug-resistant staphylococci; PNAS, Sep. 11, 2001, vol. 98, No. 19, pp. 10886-10891.
Rajarao et al., Peptide mediated delivery of green fluorescent protein into yeasts and bacteria; FEMS Microbilogy Letters, vol. 215, 2002, pp. 267-2725.
Rattan et al., Protein Synthesis, Posttranslational Modifications, and Aging; Nov. 1992, vol. 663, No. 1, pp. 48-62.
Rodloff; Medicine: Review Aritcle; Susceptible, Intermediate, and Resistant—The Intensity of Antibiotic Action; Dtsch Arztebl Int., 2008, vol. 105, No. 39, pp. 657-662.
Rudgers et al., Binding Properties of a Peptide Derived from Beta-Lactamase Inhibitory Protein; Antimicrobial Agents and Chemotherapy, De. 2001, vol. 45, No. 12, pp. 3279-3286.
Seifter et al., Analysis for protein modifications and nonprotein cofactors, Meth. Enzymol., 1990, vol. 182, pp. 626-646.
Sharma et al., Indentification and characterization of novel small molecule inhibitors of the acetyltransferase activity of *Escherichia coli* N-acetylglucosamine-1-phosphate-uridyltransferase/glucosamine-1-phosphate-acetyltransferase (GlmU); Biotechnologically Relevant Enzymes and Proteins; Appl. Microbiol., Biotechnol., 2016, vol. 100, pp. 3071-3085.
Silva et al., Beta-Lactamase inhibitor peptides as the new strategies to overcome bacterial resistance, Drugs Today (Bare), 2018, vol. 54, No. 12, pp. 737-746.
Tehrani et al., Beta-lactam/beta-lactamase inhibitor combinations: an updae: Med. Chem. Commun., 2018, vol. 9, pp. 1439-1456.
Walker et al., Biotinylation Facilitates the Uptake of Large Peptides by *Escherichia coli* and Other Gram-Negative Bacteria; Applied and Environmental Microbiology, Apr. 2005, vol. 71, No. 4, pp. 1850-1855.

* cited by examiner

SEQUENCE LISTING

```
<160> NUMBER OF SEQ ID NOS: 86

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = X1, wherein X1 is independently selected
      from K, R, or H.
```

```
<220> FEATURE:
<221> NAME/KEY: MISC_FEATURE
<222> LOCATION: (2)..(2)
<223> OTHER INFORMATION: X = X0, wherein X0 is any standard amino acid.
<220> FEATURE:
<221> NAME/KEY: MISC_FEATURE
<222> LOCATION: (3)..(3)
<223> OTHER INFORMATION: X = X2, wherein X2 is independently selected
      from Y or F.
<220> FEATURE:
<221> NAME/KEY: MISC_FEATURE
<222> LOCATION: (4)..(4)
<223> OTHER INFORMATION: X = X3, wherein X3 is independently selected
      from V, L, or I.
<220> FEATURE:
<221> NAME/KEY: MISC_FEATURE
<222> LOCATION: (5)..(5)
<223> OTHER INFORMATION: X = X0, wherein X0 is any standard amino acid.
<220> FEATURE:
<221> NAME/KEY: MISC_FEATURE
<222> LOCATION: (6)..(6)
<223> OTHER INFORMATION: X = X0, wherein X0 is any standard amino acid.
<220> FEATURE:
<221> NAME/KEY: MISC_FEATURE
<222> LOCATION: (7)..(7)
<223> OTHER INFORMATION: X = X4, wherein X4 is independently selected
      from V, L, I, or A.
<220> FEATURE:
<221> NAME/KEY: MISC_FEATURE
<222> LOCATION: (9)..(9)
<223> OTHER INFORMATION: X = X0, wherein X0 is any standard amino acid.
<220> FEATURE:
<221> NAME/KEY: MISC_FEATURE
<222> LOCATION: (10)..(10)
<223> OTHER INFORMATION: X = X0, wherein X0 is any standard amino acid.
<220> FEATURE:
<221> NAME/KEY: MISC_FEATURE
<222> LOCATION: (11)..(11)
<223> OTHER INFORMATION: X = X0, wherein X0 is any standard amino acid.

<400> SEQUENCE: 1

Xaa Xaa Xaa Xaa Xaa Xaa Xaa Ala Xaa Xaa Xaa
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = X5, wherein X5 is independently selected
      from K, R, or H.
<220> FEATURE:
<221> NAME/KEY: MISC_FEATURE
<222> LOCATION: (2)..(2)
<223> OTHER INFORMATION: X = X0, wherein X0 is any standard amino acid.
<220> FEATURE:
<221> NAME/KEY: MISC_FEATURE
<222> LOCATION: (3)..(3)
<223> OTHER INFORMATION: X = X0, wherein X0 is any standard amino acid.
<220> FEATURE:
<221> NAME/KEY: MISC_FEATURE
<222> LOCATION: (4)..(4)
<223> OTHER INFORMATION: X = X6, wherein X6 is independently selected
      from V, L, or I.
<220> FEATURE:
<221> NAME/KEY: MISC_FEATURE
<222> LOCATION: (5)..(5)
<223> OTHER INFORMATION: X = X0, wherein X0 is any standard amino acid.
<220> FEATURE:
<221> NAME/KEY: MISC_FEATURE
<222> LOCATION: (6)..(6)
<223> OTHER INFORMATION: X = X0, wherein X0 is any standard amino acid.
<220> FEATURE:
```

<221> NAME/KEY: MISC_FEATURE
<222> LOCATION: (7)..(7)
<223> OTHER INFORMATION: X = X7, wherein X7 is independently selected from V, L, I, or A.
<220> FEATURE:
<221> NAME/KEY: MISC_FEATURE
<222> LOCATION: (9)..(9)
<223> OTHER INFORMATION: X = X0, wherein X0 is any standard amino acid.
<220> FEATURE:
<221> NAME/KEY: MISC_FEATURE
<222> LOCATION: (10)..(10)
<223> OTHER INFORMATION: X = X0, wherein X0 is any standard amino acid.

<400> SEQUENCE: 2

Xaa Xaa Xaa Xaa Xaa Xaa Xaa Ala Xaa Xaa
1 5 10

<210> SEQ ID NO 3
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = X8, wherein X8 is independently selected from K, R, or H.
<220> FEATURE:
<221> NAME/KEY: MISC_FEATURE
<222> LOCATION: (2)..(2)
<223> OTHER INFORMATION: X = X9, wherein X9 is independently selected from T or S.
<220> FEATURE:
<221> NAME/KEY: MISC_FEATURE
<222> LOCATION: (3)..(3)
<223> OTHER INFORMATION: X = X0, wherein X0 is any standard amino acid.
<220> FEATURE:
<221> NAME/KEY: MISC_FEATURE
<222> LOCATION: (4)..(4)
<223> OTHER INFORMATION: X = X0, wherein X0 is any standard amino acid.
<220> FEATURE:
<221> NAME/KEY: MISC_FEATURE
<222> LOCATION: (5)..(5)
<223> OTHER INFORMATION: X = X10, wherein X10 is independently selected from V, L, or I.
<220> FEATURE:
<221> NAME/KEY: MISC_FEATURE
<222> LOCATION: (6)..(6)
<223> OTHER INFORMATION: X = X0, wherein X0 is any standard amino acid.
<220> FEATURE:
<221> NAME/KEY: MISC_FEATURE
<222> LOCATION: (7)..(7)
<223> OTHER INFORMATION: X = X0, wherein X0 is any standard amino acid.
<220> FEATURE:
<221> NAME/KEY: MISC_FEATURE
<222> LOCATION: (8)..(8)
<223> OTHER INFORMATION: X = X11, wherein X11 is independently selected from V, L, I, or A.
<220> FEATURE:
<221> NAME/KEY: MISC_FEATURE
<222> LOCATION: (10)..(10)
<223> OTHER INFORMATION: X = X0, wherein X0 is any standard amino acid.

<400> SEQUENCE: 3

Xaa Xaa Xaa Xaa Xaa Xaa Xaa Xaa Ala Xaa
1 5 10

<210> SEQ ID NO 4
<211> LENGTH: 11
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: X = X0, wherein X0 is any standard amino acid.
<220> FEATURE:
<221> NAME/KEY: MISC_FEATURE
<222> LOCATION: (2)..(2)
<223> OTHER INFORMATION: X = X0, wherein X0 is any standard amino acid.
<220> FEATURE:
<221> NAME/KEY: MISC_FEATURE
<222> LOCATION: (3)..(3)
<223> OTHER INFORMATION: X = X0, wherein X0 is any standard amino acid.
<220> FEATURE:
<221> NAME/KEY: MISC_FEATURE
<222> LOCATION: (4)..(4)
<223> OTHER INFORMATION: X = X0, wherein X0 is any standard amino acid.
<220> FEATURE:
<221> NAME/KEY: MISC_FEATURE
<222> LOCATION: (5)..(5)
<223> OTHER INFORMATION: X = X12, wherein X12 is independently selected
      from D or E.
<220> FEATURE:
<221> NAME/KEY: MISC_FEATURE
<222> LOCATION: (6)..(6)
<223> OTHER INFORMATION: X = X13, wherein X13 is independently selected
      from Y or F.
<220> FEATURE:
<221> NAME/KEY: MISC_FEATURE
<222> LOCATION: (7)..(7)
<223> OTHER INFORMATION: X = X0, wherein X0 is any standard amino acid.
<220> FEATURE:
<221> NAME/KEY: MISC_FEATURE
<222> LOCATION: (8)..(8)
<223> OTHER INFORMATION: X = X14, wherein X14 is independently selected
      from K, R, or H.
<220> FEATURE:
<221> NAME/KEY: MISC_FEATURE
<222> LOCATION: (10)..(10)
<223> OTHER INFORMATION: X = X0, wherein X0 is any standard amino acid.
<220> FEATURE:
<221> NAME/KEY: MISC_FEATURE
<222> LOCATION: (11)..(11)
<223> OTHER INFORMATION: X = X0, wherein X0 is any standard amino acid.

<400> SEQUENCE: 4

Xaa Xaa Xaa Xaa Xaa Xaa Xaa Xaa Ser Xaa Xaa
1               5                   10


<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Lys Thr Tyr Leu Ala Gln Ala Ala Ala Thr Gly
1               5                   10


<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

His Ser Gly Val Ala Ser Ala Ala Ala Gly
1               5                   10


<210> SEQ ID NO 7
<211> LENGTH: 10
<212> TYPE: PRT
<213> ORGANISM: Artificial Sequence
```

<220> FEATURE:
<223> OTHER INFORMATION: Synthetic

<400> SEQUENCE: 7

Lys Thr Phe Val Val Arg Ala Leu Ala Ser
1 5 10

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Gly Gly Ser Gly Asp Phe Ala Arg Ser Ser Tyr
1 5 10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Lys Phe Phe Lys Phe Phe Lys Phe Phe Lys
1 5 10

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Cys Phe Phe Lys Asp Glu Leu
1 5

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Lys Lys Leu Phe Lys Lys Ile Leu Lys Tyr Leu
1 5 10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Gly Arg Arg Arg Arg Arg Arg Arg Arg Arg Pro Pro Gln
1 5 10

<210> SEQ ID NO 13
<211> LENGTH: 22
<212> TYPE: PRT
<213> ORGANISM: Artificial Sequence
<220> FEATURE:

<223> OTHER INFORMATION: Synthetic

<400> SEQUENCE: 13

```
Lys Lys Leu Phe Lys Lys Ile Leu Lys Tyr Leu Lys Lys Leu Phe Lys
1               5                   10                  15

Lys Ile Leu Lys Tyr Leu
            20
```

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

```
Thr Arg Gln Ala Arg Arg Asn Arg Arg Arg Arg Trp Arg Glu Arg Gln
1               5                   10                  15

Arg
```

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

```
Arg Arg Arg Arg Arg Arg Arg Arg Arg
1               5
```

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

```
Arg Arg Arg Arg Arg Arg Arg Arg Arg Arg Arg Arg
1               5                   10
```

<210> SEQ ID NO 17
<211> LENGTH: 18
<212> TYPE: PRT
<213> ORGANISM: Artificial Sequence
<220> FEATURE:
<223> OTHER INFORMATION: Synthetic

<400> SEQUENCE: 17

```
Lys His Lys His Lys His Lys His Lys His Lys His Lys His Lys His
1               5                   10                  15

Lys His
```

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

```
Lys Lys Lys Lys Lys Lys Lys Lys Lys
1               5
```

<210> SEQ ID NO 19
<211> LENGTH: 18
<212> TYPE: PRT
<213> ORGANISM: Artificial Sequence
<220> FEATURE:
<223> OTHER INFORMATION: Synthetic

<400> SEQUENCE: 19

Lys Lys Lys Lys Lys Lys Lys Lys Lys Lys Lys Lys Lys Lys Lys Lys
1               5                   10                  15

Lys Lys

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

Arg Gln Ile Lys Ile Phe Phe Gln Asn Arg Arg Met Lys Phe Lys Lys
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

Arg Lys Lys Arg Arg Arg Glu Ser Arg Lys Lys Arg Arg Arg Glu Ser
1               5                   10                  15

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Arg Lys Arg Lys Lys Arg Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Arg Lys Lys Arg Arg Gln Arg Arg Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Arg Arg Arg Gln Arg Arg Lys Lys Arg
1               5

<210> SEQ ID NO 25
<211> LENGTH: 16
<212> TYPE: PRT
<213> ORGANISM: Artificial Sequence
<220> FEATURE:
<223> OTHER INFORMATION: Synthetic

<400> SEQUENCE: 25

Gly Leu Arg Lys Arg Leu Arg Lys Phe Arg Asn Lys Ile Lys Glu Lys
1 5 10 15

<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Lys Ala Leu Lys Lys Leu Leu Ala Lys Trp Leu Ala Ala Ala Lys Ala
1 5 10 15

Leu Leu

<210> SEQ ID NO 27
<211> LENGTH: 18
<212> TYPE: PRT
<213> ORGANISM: Artificial Sequence
<220> FEATURE:
<223> OTHER INFORMATION: Synthetic

<400> SEQUENCE: 27

Gln Leu Ala Leu Gln Leu Ala Leu Gln Ala Leu Gln Ala Ala Leu Gln
1 5 10 15

Leu Ala

<210> SEQ ID NO 28
<211> LENGTH: 18
<212> TYPE: PRT
<213> ORGANISM: Artificial Sequence
<220> FEATURE:
<223> OTHER INFORMATION: Synthetic

<400> SEQUENCE: 28

Leu Lys Thr Leu Ala Thr Ala Leu Thr Lys Leu Ala Lys Thr Leu Thr
1 5 10 15

Thr Leu

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Arg Ala Trp Met Arg Trp Tyr Ser Pro Thr Thr Arg Arg Tyr Gly
1 5 10 15

<210> SEQ ID NO 30
<211> LENGTH: 18
<212> TYPE: PRT
<213> ORGANISM: Artificial Sequence
<220> FEATURE:
<223> OTHER INFORMATION: Synthetic

<400> SEQUENCE: 30

```
Leu Leu Ile Ile Leu Arg Arg Arg Ile Arg Lys Gln Ala His Ala His
1               5                   10                  15

Ser Lys
```

<210> SEQ ID NO 31
<211> LENGTH: 16
<212> TYPE: PRT
<213> ORGANISM: Artificial Sequence
<220> FEATURE:
<223> OTHER INFORMATION: Synthetic

<400> SEQUENCE: 31

```
Arg Gln Ile Arg Ile Trp Phe Gln Asn Arg Arg Met Arg Trp Arg Arg
1               5                   10                  15
```

<210> SEQ ID NO 32
<211> LENGTH: 22
<212> TYPE: PRT
<213> ORGANISM: Artificial Sequence
<220> FEATURE:
<223> OTHER INFORMATION: Synthetic

<400> SEQUENCE: 32

```
Met Val Thr Val Leu Phe Arg Arg Leu Arg Ile Arg Arg Ala Cys Gly
1               5                   10                  15

Pro Pro Arg Val Arg Val
            20
```

<210> SEQ ID NO 33
<211> LENGTH: 16
<212> TYPE: PRT
<213> ORGANISM: Artificial Sequence
<220> FEATURE:
<223> OTHER INFORMATION: Synthetic

<400> SEQUENCE: 33

```
Arg Gln Ile Lys Ile Trp Phe Gln Asn Arg Arg Met Lys Trp Lys Lys
1               5                   10                  15
```

<210> SEQ ID NO 34
<211> LENGTH: 18
<212> TYPE: PRT
<213> ORGANISM: Artificial Sequence
<220> FEATURE:
<223> OTHER INFORMATION: Synthetic

<400> SEQUENCE: 34

```
Val Arg Leu Pro Pro Pro Val Arg Leu Pro Pro Pro Val Arg Leu Pro
1               5                   10                  15

Pro Pro
```

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

```
Leu Leu Leu Phe Leu Leu Lys Lys Arg Lys Lys Arg Lys Tyr
1               5                   10
```

<210> SEQ ID NO 36
<211> LENGTH: 23
<212> TYPE: PRT
<213> ORGANISM: Artificial Sequence
<220> FEATURE:
<223> OTHER INFORMATION: Synthetic

<400> SEQUENCE: 36

```
Ser Tyr Phe Ile Leu Arg Arg Arg Arg Lys Arg Phe Pro Tyr Phe Phe
1               5                   10                  15

Thr Asp Val Arg Val Ala Ala
            20
```

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

```
Arg Ala Gly Leu Gln Phe Pro Val Gly Arg Val His Arg Leu Leu Arg
1               5                   10                  15

Lys
```

<210> SEQ ID NO 38
<211> LENGTH: 18
<212> TYPE: PRT
<213> ORGANISM: Artificial Sequence
<220> FEATURE:
<223> OTHER INFORMATION: Synthetic

<400> SEQUENCE: 38

```
Ile Ala Ala Arg Ile Lys Leu Arg Ser Arg Gln His Ile Lys Leu Arg
1               5                   10                  15

His Leu
```

<210> SEQ ID NO 39
<211> LENGTH: 23
<212> TYPE: PRT
<213> ORGANISM: Artificial Sequence
<220> FEATURE:
<223> OTHER INFORMATION: Synthetic

<400> SEQUENCE: 39

```
Ser Tyr Asp Asp Leu Arg Arg Arg Arg Lys Arg Phe Pro Tyr Phe Phe
1               5                   10                  15

Thr Asp Val Arg Val Ala Ala
            20
```

<210> SEQ ID NO 40
<211> LENGTH: 26
<212> TYPE: PRT
<213> ORGANISM: Artificial Sequence
<220> FEATURE:
<223> OTHER INFORMATION: Synthetic

<400> SEQUENCE: 40

```
Lys Lys Ala Leu Leu Ala Leu Ala Leu His His Leu Ala His Leu Ala
1               5                   10                  15

Leu His Leu Ala Leu Ala Leu Lys Lys Ala
            20                  25
```

<210> SEQ ID NO 41

<211> LENGTH: 20
<212> TYPE: PRT
<213> ORGANISM: Artificial Sequence
<220> FEATURE:
<223> OTHER INFORMATION: Synthetic

<400> SEQUENCE: 41

```
Gly Leu Phe Lys Ala Leu Leu Lys Leu Leu Lys Ser Leu Trp Lys Leu
1               5                   10                  15

Leu Leu Lys Ala
            20
```

<210> SEQ ID NO 42
<211> LENGTH: 27
<212> TYPE: PRT
<213> ORGANISM: Artificial Sequence
<220> FEATURE:
<223> OTHER INFORMATION: Synthetic

<400> SEQUENCE: 42

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 43
<211> LENGTH: 40
<212> TYPE: PRT
<213> ORGANISM: Artificial Sequence
<220> FEATURE:
<223> OTHER INFORMATION: Synthetic

<400> SEQUENCE: 43

```
Gly Leu Phe Lys Ala Leu Leu Lys Leu Leu Lys Ser Leu Trp Lys Leu
1               5                   10                  15

Leu Leu Lys Ala Gly Leu Phe Lys Ala Leu Leu Lys Leu Leu Lys Ser
            20                  25                  30

Leu Trp Lys Leu Leu Leu Lys Ala
        35                  40
```

<210> SEQ ID NO 44
<211> LENGTH: 16
<212> TYPE: PRT
<213> ORGANISM: Artificial Sequence
<220> FEATURE:
<223> OTHER INFORMATION: Synthetic

<400> SEQUENCE: 44

```
Arg Gln Ile Lys Ile Trp Phe Pro Asn Arg Arg Met Lys Trp Lys Lys
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

```
Gln Ile Lys Ile Trp Phe Gln Asn Arg Arg Met Lys Trp Lys Lys
1               5                   10                  15
```

<210> SEQ ID NO 46
<211> LENGTH: 13
<212> TYPE: PRT

<213> ORGANISM: Artificial Sequence
<220> FEATURE:
<223> OTHER INFORMATION: Synthetic

<400> SEQUENCE: 46

Lys Met Asp Cys Arg Trp Arg Trp Lys Cys Cys Lys Lys
1 5 10

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Met Asp Cys Arg Trp Arg Trp Lys Cys Cys Lys Lys
1 5 10

<210> SEQ ID NO 48
<211> LENGTH: 14
<212> TYPE: PRT
<213> ORGANISM: Artificial Sequence
<220> FEATURE:
<223> OTHER INFORMATION: Synthetic

<400> SEQUENCE: 48

Lys Cys Gly Cys Arg Trp Arg Trp Lys Cys Gly Cys Lys Lys
1 5 10

<210> SEQ ID NO 49
<211> LENGTH: 10
<212> TYPE: PRT
<213> ORGANISM: Artificial Sequence
<220> FEATURE:
<223> OTHER INFORMATION: Synthetic

<400> SEQUENCE: 49

Cys Arg Trp Arg Trp Lys Cys Cys Lys Lys
1 5 10

<210> SEQ ID NO 50
<211> LENGTH: 22
<212> TYPE: PRT
<213> ORGANISM: Artificial Sequence
<220> FEATURE:
<223> OTHER INFORMATION: Synthetic

<400> SEQUENCE: 50

Thr Lys Arg Arg Ile Thr Pro Lys Asp Val Ile Asp Val Arg Ser Val
1 5 10 15

Thr Thr Glu Ile Asn Thr
20

<210> SEQ ID NO 51
<211> LENGTH: 26
<212> TYPE: PRT
<213> ORGANISM: Artificial Sequence
<220> FEATURE:
<223> OTHER INFORMATION: Synthetic

<400> SEQUENCE: 51

Ala Glu Lys Val Asp Pro Val Lys Leu Asn Leu Thr Leu Ser Ala Ala
1 5 10 15

Ala Glu Ala Leu Thr Gly Leu Gly Asp Lys
20 25

<210> SEQ ID NO 52
<211> LENGTH: 22
<212> TYPE: PRT
<213> ORGANISM: Artificial Sequence
<220> FEATURE:
<223> OTHER INFORMATION: Synthetic

<400> SEQUENCE: 52

Thr Lys Arg Arg Ile Thr Pro Lys Asp Val Ile Asp Val Arg Ser Val
1 5 10 15

Thr Thr Lys Ile Asn Thr
20

<210> SEQ ID NO 53
<211> LENGTH: 28
<212> TYPE: PRT
<213> ORGANISM: Artificial Sequence
<220> FEATURE:
<223> OTHER INFORMATION: Synthetic

<400> SEQUENCE: 53

His His His His His His Thr Lys Arg Arg Ile Thr Pro Lys Asp Val
1 5 10 15

Ile Asp Val Arg Ser Val Thr Thr Glu Ile Asn Thr
20 25

<210> SEQ ID NO 54
<211> LENGTH: 25
<212> TYPE: PRT
<213> ORGANISM: Artificial Sequence
<220> FEATURE:
<223> OTHER INFORMATION: Synthetic

<400> SEQUENCE: 54

Gly Thr Lys Met Ile Phe Val Gly Ile Lys Lys Lys Glu Glu Arg Ala
1 5 10 15

Asp Leu Ile Ala Tyr Leu Lys Lys Ala
20 25

<210> SEQ ID NO 55
<211> LENGTH: 22
<212> TYPE: PRT
<213> ORGANISM: Artificial Sequence
<220> FEATURE:
<223> OTHER INFORMATION: Synthetic

<400> SEQUENCE: 55

Lys Cys Phe Gln Trp Gln Arg Asn Met Arg Lys Val Arg Gly Pro Pro
1 5 10 15

Val Ser Cys Ile Lys Arg
20

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Glu Glu Glu Ala Ala Gly Arg Lys Arg Lys Lys Arg Thr
1 5 10

<210> SEQ ID NO 57
<211> LENGTH: 15
<212> TYPE: PRT
<213> ORGANISM: Artificial Sequence
<220> FEATURE:
<223> OTHER INFORMATION: Synthetic

<400> SEQUENCE: 57

Phe Leu Gly Lys Lys Phe Lys Lys Tyr Phe Leu Gln Leu Leu Lys
1 5 10 15

<210> SEQ ID NO 58
<211> LENGTH: 23
<212> TYPE: PRT
<213> ORGANISM: Artificial Sequence
<220> FEATURE:
<223> OTHER INFORMATION: Synthetic

<400> SEQUENCE: 58

Phe Leu Ile Phe Ile Arg Val Ile Cys Ile Val Ile Ala Lys Leu Lys
1 5 10 15

Ala Asn Leu Met Cys Lys Thr
20

<210> SEQ ID NO 59
<211> LENGTH: 16
<212> TYPE: PRT
<213> ORGANISM: Artificial Sequence
<220> FEATURE:
<223> OTHER INFORMATION: Synthetic

<400> SEQUENCE: 59

Tyr Ile Val Leu Arg Arg Arg Arg Lys Arg Val Asn Thr Lys Arg Ser
1 5 10 15

<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

Lys Thr Val Leu Leu Arg Lys Leu Leu Lys Leu Leu Val Arg Lys Ile
1 5 10 15

<210> SEQ ID NO 61
<211> LENGTH: 16
<212> TYPE: PRT
<213> ORGANISM: Artificial Sequence
<220> FEATURE:
<223> OTHER INFORMATION: Synthetic

<400> SEQUENCE: 61

Leu Leu Lys Lys Arg Lys Val Val Arg Leu Ile Lys Phe Leu Leu Lys
1 5 10 15

<210> SEQ ID NO 62
<211> LENGTH: 16
<212> TYPE: PRT
<213> ORGANISM: Artificial Sequence
<220> FEATURE:
<223> OTHER INFORMATION: Synthetic

<400> SEQUENCE: 62

Lys Lys Ile Cys Thr Arg Lys Pro Arg Phe Met Ser Ala Trp Ala Gln
1 5 10 15

<210> SEQ ID NO 63
<211> LENGTH: 23
<212> TYPE: PRT
<213> ORGANISM: Artificial Sequence
<220> FEATURE:
<223> OTHER INFORMATION: Synthetic

<400> SEQUENCE: 63

Gly Ile Gly Lys Phe Leu His Ser Ala Lys Lys Trp Gly Lys Ala Phe
1 5 10 15

Val Gly Gln Ile Met Asn Cys
20

<210> SEQ ID NO 64
<211> LENGTH: 21
<212> TYPE: PRT
<213> ORGANISM: Artificial Sequence
<220> FEATURE:
<223> OTHER INFORMATION: Synthetic

<400> SEQUENCE: 64

Lys Phe Phe Lys Phe Phe Lys Phe Phe Lys Lys Thr Tyr Leu Ala Gln
1 5 10 15

Ala Ala Ala Thr Gly
20

<210> SEQ ID NO 65
<211> LENGTH: 18
<212> TYPE: PRT
<213> ORGANISM: Artificial Sequence
<220> FEATURE:
<223> OTHER INFORMATION: Synthetic

<400> SEQUENCE: 65

Cys Phe Phe Lys Asp Glu Leu Lys Thr Tyr Leu Ala Gln Ala Ala Ala
1 5 10 15

Thr Gly

<210> SEQ ID NO 66
<211> LENGTH: 22
<212> TYPE: PRT
<213> ORGANISM: Artificial Sequence
<220> FEATURE:
<223> OTHER INFORMATION: Synthetic

<400> SEQUENCE: 66

Lys Lys Leu Phe Lys Lys Ile Leu Lys Tyr Leu Lys Thr Tyr Leu Ala
1 5 10 15

Gln Ala Ala Ala Thr Gly
20

<210> SEQ ID NO 67
<211> LENGTH: 20
<212> TYPE: PRT
<213> ORGANISM: Artificial Sequence
<220> FEATURE:
<223> OTHER INFORMATION: Synthetic

<400> SEQUENCE: 67

Lys Thr Phe Val Val Arg Ala Leu Ala Ser Cys Lys Phe Phe Lys Phe
1 5 10 15

Phe Lys Phe Phe
20

<210> SEQ ID NO 68
<211> LENGTH: 24
<212> TYPE: PRT
<213> ORGANISM: Artificial Sequence
<220> FEATURE:
<223> OTHER INFORMATION: Synthetic

<400> SEQUENCE: 68

Gly Arg Arg Arg Arg Arg Arg Arg Arg Arg Pro Pro Gln Lys Thr Tyr
1 5 10 15

Leu Ala Gln Ala Ala Ala Thr Gly
20

<210> SEQ ID NO 69
<211> LENGTH: 20
<212> TYPE: PRT
<213> ORGANISM: Artificial Sequence
<220> FEATURE:
<223> OTHER INFORMATION: Synthetic

<400> SEQUENCE: 69

Lys Phe Phe Lys Phe Phe Lys Phe Phe Lys His Ser Gly Val Ala Ser
1 5 10 15

Ala Ala Ala Gly
20

<210> SEQ ID NO 70
<211> LENGTH: 17
<212> TYPE: PRT
<213> ORGANISM: Artificial Sequence
<220> FEATURE:
<223> OTHER INFORMATION: Synthetic

<400> SEQUENCE: 70

Cys Phe Phe Lys Asp Glu Leu His Ser Gly Val Ala Ser Ala Ala Ala
1 5 10 15

Gly

<210> SEQ ID NO 71
<211> LENGTH: 21
<212> TYPE: PRT
<213> ORGANISM: Artificial Sequence
<220> FEATURE:
<223> OTHER INFORMATION: Synthetic

<400> SEQUENCE: 71

Lys Lys Leu Phe Lys Lys Ile Leu Lys Tyr Leu His Ser Gly Val Ala
1 5 10 15

Ser Ala Ala Ala Gly
20

<210> SEQ ID NO 72
<211> LENGTH: 23
<212> TYPE: PRT
<213> ORGANISM: Artificial Sequence
<220> FEATURE:
<223> OTHER INFORMATION: Synthetic

<400> SEQUENCE: 72

Gly Arg Arg Arg Arg Arg Arg Arg Arg Arg Pro Pro Gln His Ser Gly
1 5 10 15

Val Ala Ser Ala Ala Ala Gly
20

<210> SEQ ID NO 73
<211> LENGTH: 20
<212> TYPE: PRT
<213> ORGANISM: Artificial Sequence
<220> FEATURE:
<223> OTHER INFORMATION: Synthetic

<400> SEQUENCE: 73

Lys Phe Phe Lys Phe Phe Lys Phe Phe Lys Lys Thr Phe Val Val Arg
1 5 10 15

Ala Leu Ala Ser
20

<210> SEQ ID NO 74
<211> LENGTH: 17
<212> TYPE: PRT
<213> ORGANISM: Artificial Sequence
<220> FEATURE:
<223> OTHER INFORMATION: Synthetic

<400> SEQUENCE: 74

Cys Phe Phe Lys Asp Glu Leu Lys Thr Phe Val Val Arg Ala Leu Ala
1 5 10 15

Ser

<210> SEQ ID NO 75
<211> LENGTH: 21
<212> TYPE: PRT
<213> ORGANISM: Artificial Sequence
<220> FEATURE:
<223> OTHER INFORMATION: Synthetic

<400> SEQUENCE: 75

Lys Lys Leu Phe Lys Lys Ile Leu Lys Tyr Leu Lys Thr Phe Val Val
1 5 10 15

Arg Ala Leu Ala Ser
20

<210> SEQ ID NO 76
<211> LENGTH: 23
<212> TYPE: PRT
<213> ORGANISM: Artificial Sequence
<220> FEATURE:
<223> OTHER INFORMATION: Synthetic

<400> SEQUENCE: 76

Gly Arg Arg Arg Arg Arg Arg Arg Arg Arg Pro Pro Gln Lys Thr Phe
1 5 10 15

Val Val Arg Ala Leu Ala Ser
20

<210> SEQ ID NO 77
<211> LENGTH: 21
<212> TYPE: PRT
<213> ORGANISM: Artificial Sequence
<220> FEATURE:
<223> OTHER INFORMATION: Synthetic

<400> SEQUENCE: 77

Lys Phe Phe Lys Phe Phe Lys Phe Phe Lys Gly Gly Ser Gly Asp Phe
1 5 10 15

Ala Arg Ser Ser Tyr
20

```
<210> SEQ ID NO 78
<211> LENGTH: 18
<212> TYPE: PRT
<213> ORGANISM: Artificial Sequence
<220> FEATURE:
<223> OTHER INFORMATION: Synthetic

<400> SEQUENCE: 78

Cys Phe Phe Lys Asp Glu Leu Gly Gly Ser Gly Asp Phe Ala Arg Ser
1               5                   10                  15

Ser Tyr


<210> SEQ ID NO 79
<211> LENGTH: 22
<212> TYPE: PRT
<213> ORGANISM: Artificial Sequence
<220> FEATURE:
<223> OTHER INFORMATION: Synthetic

<400> SEQUENCE: 79

Lys Lys Leu Phe Lys Lys Ile Leu Lys Tyr Leu Gly Gly Ser Gly Asp
1               5                   10                  15

Phe Ala Arg Ser Ser Tyr
            20


<210> SEQ ID NO 80
<211> LENGTH: 24
<212> TYPE: PRT
<213> ORGANISM: Artificial Sequence
<220> FEATURE:
<223> OTHER INFORMATION: Synthetic

<400> SEQUENCE: 80

Gly Arg Arg Arg Arg Arg Arg Arg Arg Arg Pro Pro Gln Gly Gly Ser
1               5                   10                  15

Gly Asp Phe Ala Arg Ser Ser Tyr
            20


<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Gly Arg Ala Tyr Asn Ala Val Tyr His Asp
1               5                   10


<210> SEQ ID NO 82
<211> LENGTH: 11
<212> TYPE: PRT
<213> ORGANISM: Artificial Sequence
<220> FEATURE:
<223> OTHER INFORMATION: Synthetic

<400> SEQUENCE: 82

Phe Asn Ser Glu Arg Tyr Ser Ser Ser Arg Pro
1               5                   10


<210> SEQ ID NO 83
<211> LENGTH: 12
<212> TYPE: PRT
<213> ORGANISM: Artificial Sequence
```

-continued

```
<220> FEATURE:
<223> OTHER INFORMATION: Synthetic

<400> SEQUENCE: 83

Ser Gly Arg Ala Val Tyr Tyr Gly Asp Val Thr Gly
1               5                   10


<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

Thr Thr Arg Lys Leu Tyr Glu Lys Lys Leu Leu
1               5                   10


<210> SEQ ID NO 85
<211> LENGTH: 10
<212> TYPE: PRT
<213> ORGANISM: Artificial Sequence
<220> FEATURE:
<223> OTHER INFORMATION: Synthetic

<400> SEQUENCE: 85

Gly Arg Arg Asp Lys Ile Gly Thr Ile Arg
1               5                   10


<210> SEQ ID NO 86
<211> LENGTH: 11
<212> TYPE: PRT
<213> ORGANISM: Artificial Sequence
<220> FEATURE:
<223> OTHER INFORMATION: Synthetic

<400> SEQUENCE: 86

Ile Asp Met Asp Asp Tyr Asp Ala Phe Arg Thr
1               5                   10
```

PEPTIDE INHIBITORS OF BETA-LACTAMASE AGAINST ANTIBIOTIC RESISTANCE

CROSS-REFERENCE TO RELATED APPLICATIONS

This application claims priority to International Application Number PCT/US2021/035849, filed on Jun. 4, 2021, which claims the benefit to U.S. Provisional Application Ser. No. 63/034,528, filed Jun. 4, 2020, each of which is incorporated herein by reference in its entirety.

STATEMENT REGARDING FEDERALLY SPONSORED RESEARCH OR DEVELOPMENT

This invention was made with Government support under grant numbers R35 GM136409 and R01 GM109980 awarded by the National Institutes of Health. The government has certain rights in the invention.

INCORPORATION OF SEQUENCE LISTING

A computer readable form of the Sequence Listing containing the file named “PCTSeq080052807501.txt”, which is 26,082 bytes in size (as measured in MICROSOFT WINDOWS® EXPLORER), is provided herein and is herein incorporated by reference. This Sequence Listing consists of SEQ ID NOs:1-86.

FIELD OF THE INVENTION

The present invention relates to new peptide inhibitors against beta-lactam resistance that can improve the efficacy of currently available antibiotics. Methods of using for treating bacterial infections are also disclosed.

BACKGROUND OF THE INVENTION

The emergence of antibiotic resistance poses an urgent medical problem worldwide. The U.S. Centers for Disease Control and Prevention (CDC) estimates that more than 2.8 million infections and 35,000 deaths each year in the United States. The Organization for Economic Co-operation and Development (OECD) predicted that 2.4 million deaths in Europe, North America and Australia from infections by resistant microorganisms in the next 30 years will cost up to US$3.5 billion per year. β-lactam antibiotics were the first class of natural antibiotics to be developed and remain a major class of drugs in clinical use. However, resistance has developed against β-lactam and production of β-lactamase is the most prominent mechanism of resistance among certain bacteria.

Selective β-lactamase inhibitors have been developed and co-administered with antibiotics to overcome resistance. Augmentin (amoxicillin/clavulanate) has achieved huge commercial success. In 2017, Augmentin (amoxicillin/clavulanate) had more about 6.4 million US prescriptions (clincalc.com/DrugStats/), and GSK alone achieved £587 million sale. However, resistance to the inhibitors have been developing in multi-drug resistance (MDR) bacteria. For example, extended-spectrum beta-lactamase (ESBL)-producing Enterobacteriaceae is categorized as a serious threat by CDC, with 197,400 cases identified in US hospitalized patients in 2017. There is tremendous interest and effort in developing 0-lactamase inhibitors due to clinical needs. Most of the effort focus on small-molecule chemical compounds. There are few studies on developing other biological agents such as peptides as inhibitors, and the reported peptides have very low inhibitory activity in vitro and no reported inhibitory activity in vivo. Peptide drugs constitute an important source for drug development that cannot be substituted by small molecules, such as in cases that involve a very large or quite flat targeting pocket. Advances of synthetic strategies also significantly improve the potential of peptide drugs by extending half-life or improving solubility.

BRIEF SUMMARY OF THE INVENTION

Provided herein are antibacterial peptide having a binding motif comprising an amino acid sequence selected from the group consisting of: (a) $X_1$-$X_0$-$X_2$-$X_3$-$X_0$-$X_0$-$X_4$-A-$X_0$-$X_0$-$X_0$ (SEQ ID NO: 1), (b) $X_5$-$X_0$-$X_0$-$X_6$-$X_0$-$X_0$-$X_7$-A-$X_0$-$X_0$ (SEQ ID NO: 2), (c) $X_8$-$X_9$-$X_0$-$X_0$-$X_{10}$-$X_0$-$X_0$-$X_{11}$-A-$X_0$ (SEQ ID NO: 3), and (d) $X_0$-$X_0$-$X_0$-$X_0$-$X_{12}$-$X_{13}$-$X_0$-$X_{14}$-S-$X_0$-$X_0$ (SEQ ID NO: 4) wherein each $X_0$ is any standard amino acid; $X_1$, $X_5$, $X_8$ and $X_{14}$ are each independently selected from lysine (K), arginine (R) or histidine (H); $X_2$ and $X_{13}$ are each independently selected from tyrosine (Y) or phenylalanine (F); $X_3$, $X_6$, and $X_{10}$ are each independently selected from valine (V), leucine (L) or isoleucine (I); $X_4$, $X_7$, and $X_{11}$ are each independently selected from valine (V), leucine (L), isoleucine (I), or alanine (A); $X_9$ is threonine (T) or serine (S); and $X_{12}$ is aspartic acid (D) or glutamic acid (E).

Also provided are compositions comprising an antibacterial peptide described herein and a pharmaceutically acceptable carrier.

Also provided are methods of reducing a bacterial titer, the methods comprising administering the antibacterial peptide to the bacteria.

Other objects and features will be in part apparent and in part pointed out hereinafter.

DETAILED DESCRIPTION OF THE INVENTION

Figure 1:
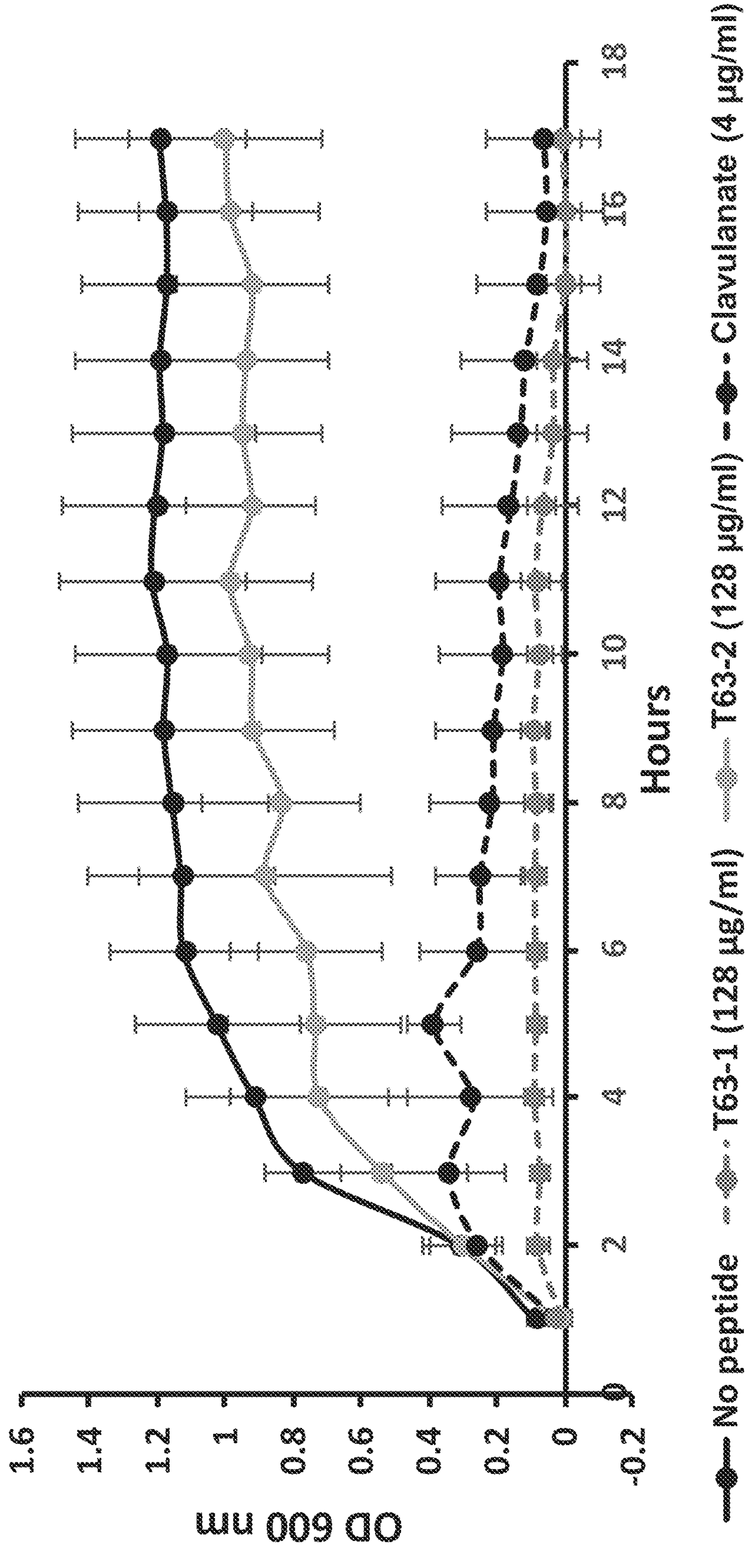
FIG. 1 shows growth curves of ATCC35218 treated with 32 μg/ml amoxicillin with peptides with different CPPs (T62-1, T63-2), control, or clavulanate.

Provided herein are peptides that can inhibit the action of beta lactamase. Certain aspects of the disclosure include novel peptide inhibitors against TEM-1 β-lactamase in *E. coli*, which will work through a different mechanism from the known small-molecule inhibitors. The class A TEM-1 lactamase is the most prevalent plasmid encoded lactamase in gram-negative bacteria. As a result, these novel peptide inhibitors could potentially replace or supplement the current β-lactamase inhibitor drugs to overcome the MDR bacterial resistance to these drugs, which will meet a significant clinical need.

Certain preferred methods and materials are described below, although methods and material similar or equivalent to those described herein can be used in practice or testing of the present invention. All publications, patent applications, patents and other references mentioned herein are incorporated by reference in their entirety. The materials, methods and examples disclosed herein are illustrative only and not intended to be limiting.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

In various embodiments, an antibacterial peptide is provided. The antibacterial peptide can comprise a binding motif comprising an amino acid sequence selected from the group consisting of: (a) $X_1$-$X_0$-$X_2$-$X_3$-$X_0$-$X_0$-$X_4$-A-$X_0$-$X_0$-$X_0$ (SEQ ID NO: 1), (b) $X_5$-$X_0$-$X_0$-$X_6$-$X_0$-$X_0$-$X_7$-A-$X_0$-$X_0$ (SEQ ID NO: 2), (c) $X_8$-$X_9$-$X_0$-$X_0$-$X_{10}$-$X_0$-$X_0$-$X_{11}$-A-$X_0$ (SEQ ID NO: 3), and (d) $X_0$-$X_0$-$X_0$-$X_0$-$X_{12}$-$X_{13}$-$X_0$-$X_{14}$-S-$X_0$-$X_0$ (SEQ ID NO: 4), wherein each $X_0$ is any standard amino acid; $X_1$, $X_5$, $X_8$ and $X_{14}$ are each independently selected from lysine (K), arginine (R) or histidine (H); $X_2$ and $X_{13}$ are each independently selected from tyrosine (Y) or phenylalanine (F); $X_3$, $X_6$, and $X_{10}$ are each independently selected from valine (V), leucine (L) or isoleucine (I); $X_4$, $X_7$, and $X_{11}$ are each independently selected from valine (V), leucine (L), isoleucine (I), or alanine (A); $X_9$ is threonine (T) or serine (S); and $X_{12}$ is aspartic acid (D) or glutamic acid (E).

Accordingly, in various embodiments, $X_1$, $X_5$, and $X_8$ can each be independently lysine (K) or histidine (H). For example, $X_1$ and $X_8$ can each be lysine (K). As a further example, $X_5$ can be histidine (H).

In various embodiments, $X_{14}$ can be arginine (R).

In various embodiments, $X_2$ can be tyrosine (Y).

In various embodiments, $X_{13}$ can be phenylalanine (F).

In additional embodiments, $X_3$, $X_6$ and $X_{10}$ can each independently be leucine (L) or valine (V). For example, $X_3$ can be leucine. As another example, $X_6$ and $X_{10}$ can each be valine (V).

In additional embodiments, $X_4$, $X_7$ and $X_{11}$ can each independently be alanine (A) or leucine (L). For example, $X_4$ and $X_7$ can each be alanine (A). As another example, $X_{11}$ can be leucine (L).

In various embodiments, $X_9$ can be threonine (T).

In various embodiments, $X_{12}$ can be aspartic acid (D).

In various embodiments, each $X_0$ can be independently selected from threonine (T), alanine (A), glutamine (Q), or glycine (G), serine (S), phenylalanine (F), valine (V), arginine (R), or tyrosine (Y). For example, each $X_0$ can be independently selected from threonine (T), alanine (A), glutamine (Q) or glycine (G). Alternatively, each $X_0$ can be independently selected from serine (S), glycine (G), or alanine (A). Alternatively, each $X_0$ can be independently selected from phenylalanine (F), valine (V), arginine (R), alanine (A), or serine (S). Alternatively, each $X_0$ can be independently selected from glycine (G), serine (S), alanine (A), or tyrosine (Y).

For example, the binding motif of the antibacterial peptide can comprise the amino acid sequence of (a), wherein $X_1$ is lysine (K), $X_2$ is tyrosine (Y), $X_3$ is leucine (L), and $X_4$ is alanine (A). For example, the amino acid sequence of (a) can comprise KTYLAQAAATG (SEQ ID NO: 5). For example, the amino acid sequence of (a) can consist of KTYLAQAAATG (SEQ ID NO: 5).

As another example, the binding motif of the antibacterial peptide can comprise the amino acid sequence of (b), wherein $X_5$ is histidine (H), $X_6$ is valine (V) and $X_7$ is alanine (A). For example, the amino acid sequence of (b) can comprise HSGVASAAAG (SEQ ID NO: 6). In another example, the amino acid sequence of (b) can consist of HSGVASAAAG (SEQ ID NO: 6).

In various embodiments, the binding motif can comprise the amino acid sequence of (c), wherein $X_8$ is lysine, $X_9$ is threonine, $X_{10}$ is valine, and $X_{11}$ is leucine. For example, the amino acid sequence of (c) can comprise KTFVVRALAS (SEQ ID NO: 7). For example, the amino acid sequence of (c) can consist of KTFVVRALAS (SEQ ID NO: 7).

In various embodiments, the binding motif can comprise the amino acid sequence of (d), wherein $X_{12}$ is aspartic acid (D), $X_{13}$ is phenylalanine (F), and $X_{14}$ is arginine (R). For example, the amino acid sequence of (d) can comprise GGSGDFARSSY (SEQ ID NO: 8). In addition, the amino acid sequence of (d) can consist of GGSGDFARSSY (SEQ ID NO: 8).

For ease of reference, the sequences which can comprise the binding motif of the antibacterial peptide are described in Table 1, below, along with their SEQ ID NOs.

TABLE 1

| Binding motifs and Illustrative Sequences thereof. | | | |
|---|---|---|---|
| Binding motif* | SEQ ID NO: | Illustrative Sequence | SEQ ID NO: |
| (K/R/H)x(Y/F)(L/I/V)X x(A/V/L/I/)Axxx | 1 | KTYLAQAAATG | 5 |
| (H/K/R)xx(V/I/L)xx(A/ L/I/V)Axx | 2 | HSGVASAAAG | 6 |
| (K/R/H)(T/S)xx(V/L/I) xx(L/I/V/A)Ax | 3 | KTFVVRALAS | 7 |
| xxxx(D/E)(F/Y)x(R/K/ H)Sxx | 4 | GGSGDFARSSY | 8 |

In any embodiment described herein, the binding motif of the antibiotic peptide can consist of any one of SEQ ID NOs: 1 to 8. In any embodiment described herein, the binding motif of the antibiotic peptide can consist of any one of SEQ ID NOs: 5 to 8.

In various embodiments, the antibiotic peptide can further comprise a cell permeating peptide (CPP). The cell permeating peptide can assist in facilitating the entry of the antibiotic peptide into the target cell (i.e., bacterium). Various cell permeating peptides are known in the art. For example, additional CPPs known in the art can be found on online databases (i.e., crdd.osdd.net/raghava/cppsite), in Oikawa et al., (Screening of a Cell-Penetrating Peptide Library in *Escherichia coli*: Relationship between Cell Penetration Efficiency and Cytotoxicity. ACS Omega 2018, 3, 16489-164), the disclosure of each is incorporated by reference in its entirety. In various embodiments, the cell permeating peptide can comprise any peptide listed in Table 2 below. In various embodiments, the cell permeating peptide can comprise or consist of any one of SEQ ID NOs: 9 to 63. For example, the cell permeating peptide can comprise or consist of any one of SEQ ID NOs: 9 to 12.

TABLE 2

| Illustrative Cell Permeating Peptides (CPPs) | |
|---|---|
| Sequence | SEQ ID NO: |
| KFFKFFKFFK | 9 |
| CFFKDEL | 10 |
| KKLFKKILKYL | 11 |
| GRRRRRRRRRPPQ | 12 |
| KKLFKKILKYLKKLFKKILKYL | 13 |
| TRQARRNRRRRWRERQR | 14 |
| RRRRRRRRR | 15 |
| RRRRRRRRRRRR | 16 |
| KHKHKHKHKHKHKHKHKH | 17 |
| KKKKKKKKK | 18 |
| KKKKKKKKKKKKKKKKKK | 19 |
| RQIKIFFQNRRMKFKK | 20 |
| RKKRRRESRKKRRRES | 21 |

TABLE 2-continued

| Illustrative Cell Permeating Peptides (CPPs) | |
|---|---|
| Sequence | SEQ ID NO: |
| GRKRKKRT | 22 |
| RKKRRQRRR | 23 |
| RRRQRRKKR | 24 |
| GLRKRLRKFRNKIKEK | 25 |
| KALKKLLAKWLAAAKALL | 26 |
| QLALQLALQALQAALQLA | 27 |
| LKTLATALTKLAKTLTTL | 28 |
| RAWMRWYSPTTRRYG | 29 |
| LLIILRRRIRKQAHAHSK | 30 |
| RQIRIWFQNRRMRWRR | 31 |
| MVTVLFRRLRIRRACGPPRVRV | 32 |
| RQIKIWFQNRRMKWKK | 33 |
| VRLPPPVRLPPPVRLPPP | 34 |
| LLLFLLKKRKKRKY | 35 |
| SYFILRRRRKRFPYFFTDVRVAA | 36 |
| RAGLQFPVGRVHRLLRK | 37 |
| IAARIKLRSRQHIKLRHL | 38 |
| SYDDLRRRRKRFPYFFTDVRVAA | 39 |
| KKALLALALHHLAHLALHLALALKK A | 40 |
| GLFKALLKLLKSLWKLLLKA | 41 |
| GWTLNSAGYLLGKINLKALAALAKK IL | 42 |
| GLFKALLKLLKSLWKLLLKAGLFKA LLKLLKSLWKL LLKA | 43 |
| RQIKIWFPNRRMKWKK | 44 |
| QIKIWFQNRRMKWKK | 45 |
| KMDCRWRWKCCKK | 46 |
| MDCRWRWKCCKK | 47 |
| KCGCRWRWKCGCKK | 48 |
| CRWRWKCCKK | 49 |
| TKRRITPKDVIDVRSVTTEINT | 50 |
| AEKVDPVKLNLTLSAAAEALTGLGD K | 51 |
| TKRRITPKDVIDVRSVTTKINT | 52 |
| HHHHHHTKRRITPKDVIDVRSVTTEI NT | 53 |
| GTKMIFVGIKKKEERADLIAYLKKA | 54 |
| KCFQWQRNMRKVRGPPVSCIKR | 55 |
| EEEAAGRKRKKRT | 56 |
| FLGKKFKKYFLQLLK | 57 |
| FLIFIRVICIVIAKLKANLMCKT | 58 |

TABLE 2-continued

Illustrative Cell Permeating Peptides (CPPs)

| Sequence | SEQ ID NO: |
|---|---|
| YIVLRRRRKRVNTKRS | 59 |
| KTVLLRKLLKLLVRKI | 60 |
| LLKKRKVVRLIKFLLK | 61 |
| KKICTRKPRFMSAWAQ | 62 |
| GIGKFLHSAKKWGKAFVGQIMNC | 63 |

Any of the binding motifs may be indirectly or directly connected with any cell wall-permeating peptides (CPP) known in the art to form an antibacterial peptide. In various embodiments, the connection between the binding motif and the CPP comprises a covalent bond, such as a peptide bond. In other embodiments, the connection between the binding motif and the CPP comprises a covalent bond that does not comprise a peptide bond. In other embodiments, the connection between the binding motif and the CPP comprises a linker of one or more atoms. Other direct or indirect linkages are possible. For example, suitable linkages are described in Lee et al., (Conjugation of Cell-Penetrating Peptides to Antimicrobial Peptides Enhances Antibacterial Activity. ACS Omega. 2019 Sep. 24; 4(13): 15694-15701) the disclosure of which is incorporated by reference in its entirety. In addition, the cell permeating peptide can be directly connected to the binding motif or may be separated by intervening amino acids. The cell permeating peptide can precede or follow the binding motif. Preferably, the cell permeating peptide links (directly or indirectly) to the N-terminus of the binding motif. For example, Table 3 provides illustrative antibacterial peptides formed from the binding motifs described above in combination with some of the cell permeating peptides described in Table 2.

TABLE 3

| Combined CPP+ Binding Peptide Sequence | SEQ ID NO: |
|---|---|
| KFFKFFKFFKKTYLAQAAATG | 64 |
| CFFKDELKTYLAQAAATG | 65 |
| KKLFKKILKYLKTYLAQAAATG | 66 |
| KTFVVRALASCKFFKFFKFF | 67 |
| GRRRRRRRRRPPQKTYLAQAAATG | 68 |
| KFFKFFKFFKHSGVASAAAG | 69 |
| CFFKDELHSGVASAAAG | 70 |
| KKLFKKILKYLHSGVASAAAG | 71 |
| GRRRRRRRRRPPQHSGVASAAAG | 72 |
| KFFKFFKFFKKTFVVRALAS | 73 |
| CFFKDELKTFVVRALAS | 74 |
| KKLFKKILKYLKTFVVRALAS | 75 |
| GRRRRRRRRRPPQKTFVVRALAS | 76 |

TABLE 3-continued

| Combined CPP+ Binding Peptide Sequence | SEQ ID NO: |
|---|---|
| KFFKFFKFFKGGSGDFARSSY | 77 |
| CFFKDELGGSGDFARSSY | 78 |
| KKLFKKILKYLGGSGDFARSSY | 79 |
| GRRRRRRRRRPPQGGSGDFARSSY | 80 |

In various embodiments, an amino acid sequence of the antibacterial peptide can comprise any one of SEQ ID NOs: 64 to 80. For example, an amino acid sequence of the antibacterial peptide can consist of any one of SEQ ID NOs: 64 to 80. For example, an amino acid sequence of the antibacterial peptide can comprise or consist of any one of SEQ ID NOs 64 to 67.

Table 4 provides exemplary antibacterial peptides designed to target both PbP2a and β-lactamase.

TABLE 4

| | Peptide sequence | SEQ ID NO: |
|---|---|---|
| T89-09 | GRAYNAVYHD | 81 |
| T89-10 | FNSERYSSSRP | 82 |
| T89-11 | SGRAVYYGDVTG | 83 |
| T89-12 | TTRKLYEKKLL | 84 |
| T89-13 | GRRDKIGTIR | 85 |
| T89-14 | IDMDDYDAFRT | 86 |

In various embodiments, an amino acid sequence of an antibacterial peptide can comprise any one of SEQ ID NOs: 81 to 86. In certain embodiments, an amino acid sequence of the antibacterial peptide can consist of any one of SEQ ID Nos: 81 to 86.

Any of the antibacterial peptides described with respect to Table 4 to may be indirectly or directly connected with any cell wall-permeating peptides (CPP) known in the art to form an antibacterial peptide, including via any of the connections and linkages described above with respect to the connections between the binding motifs and CPPs. The cell permeating peptide can precede or follow the antibacterial peptides described with respect to Table 4. Preferably, the cell permeating peptide links (directly or indirectly) to the N-terminus of the peptide. In various embodiments, an antibacterial peptide comprising or consisting of any one of SEQ ID Nos: 81 to 86 can be combined with any of the cell permeating peptides described in Table 2.

As used herein, "peptide" is understood to be an amino acid chain that is notably shorter than a full-length protein. Accordingly, in various embodiments the antibacterial peptide can have a length of about 50 amino acids or fewer, about 45 amino acids or fewer, about 40 amino acids or fewer, about 35 amino acids or fewer, about 30 amino acids or fewer, about 25 amino acids or fewer, or about 20 amino acids or fewer. For example, the peptide can have a length of about 5 amino acids or greater, 6 amino acids or greater, 7 amino acids or greater, 8 amino acids or greater, 9 amino acids or greater, 10 amino acids or greater, about 11 amino acids or greater, about 12 amino acids or greater, about 13 amino acids or greater, about 14 amino acids or greater, about 15 amino acids or greater, about 16 amino acids or greater, about 17 amino acids or greater, about 18 amino acids or greater, or about 19 amino acids or greater. For example, the peptide can have a length from about 5 to about 50 amino acids, from about 5 to about 40 amino acids, from about 5 to about 30 amino acids, from about 5 to about 25 amino acids, or from about 5 to about 20 amino acids. In additional embodiments, the peptide can have a length of about 5, about 6, about 7, about 8, about 9, about 10, about 11, about 12, about 13, about 14, about 15, about 16, about 17, or about 18 amino acids.

As discussed above, the antibacterial peptide can inhibit the activity of a (3-lactamase. Accordingly, the antibacterial peptide can bind to the β-lactamase. The β-lactamase can comprise an extended-spectrum β-lactamase. In addition, the binding of the antibacterial peptide to the β-lactamase can inhibit cleavage of a β-lactam by the β-lactamase.

In various embodiments, the β-lactamase can be expressed by a gram positive or a gram negative bacterium (bacteria).

When the β-lactamase is expressed by a gram positive bacterium, the gram positive bacterium can comprise *Staphylococcus aureus, Streptococcus pneumoniae, Bacillus subtilis, Bacillus licheniformis, Bacillus cereus, Bacillus amyloliquefaciens, Bacillus velezensis, Bacillus thuringiensis, Bacillus mycoides, Streptomyces cellulosae, Streptomyces badius, Streptomyces cacaoi, Streptomyces fradiae* (*Streptomyces roseoflavus*), *Kitasatospora aureofaciens* (*Streptomyces aureofaciens*), *Streptomyces albus* G, *Streptomyces lavendulae, Nocardia, Amycolatopsis*, Mycolicibacterium *fortuitum* (*Mycobacterium fortuitum*), *Mycobacterium tuberculosis*, or any combination thereof.

When the β-lactamase is expressed by a gram negative bacterium, the gram negative bacterium can comprise *Escherichia coli, Neisseria gonorrhoeae, Acinetobacter baumannii, Moraxella catarrhalis, Shigella, Klebsiella, Enterobacter aerogenes, Enterobacter cloacae, Proteus*, Mycolicibacterium *fortuitum* (*Mycobacterium fortuitum*), *Mycobacterium tuberculosis, Aeromonas hydrophila, Pseudomonas aeruginosa, Stenotrophomonas maltophilia* (*Pseudomonas maltophilia*), *Rhodobacter capsulatus* (*Rhodopseudomonas capsulata*), *Haemophilus influenzae, Vibrio cholerae, Citrobacter, Yersinia, Serratia, Salmonella, Kluyvera*, or any combination thereof.

In various embodiments, the β-lactamase is expressed by *Escherichia coli* ATCC 35218 or *Staphylococcus aureus.*

Methods of Producing Antibacterial Peptides

Any of the peptides described herein can be prepared using standard methods in the art. For example the peptides can be chemically synthesized via standard solid phase peptide synthesis described, for example, by Merrifield, R. B. (Solid Phase Peptide Synthesis I. The Synthesis of a Tetrapeptide. (1963) Journal of the American Chemical Society, 85, 2149-2154) the disclosure of which is incorporated by reference herein in its entirety. In various embodiments, the peptides provided herein may be modified to improve deliverability, stability, potency, or any other property important for drug delivery.

In addition, peptides can be chemically synthesized with D-amino acids, β2-amino acids, β3-amino acids, homo amino acids, gamma amino acids, peptoids, N-methyl amino acids, and other non-natural amino acid mimics and derivatives.

The peptides may be modified by either natural processes, such as posttranslational processing, or by chemical modification techniques that are well known in the art. Modifications can occur anywhere in a peptide, including the peptide backbone, the amino acid side-chains and the amino or carboxyl termini. The same type of modification may be present in the same or varying degrees at several sites in a peptide. Also, a peptide may contain many types of modifications.

Peptides may be branched, for example, as a result of ubiquitination, and they may be cyclic, with or without branching. Cyclic, branched, and branched cyclic polypeptides may result from posttranslation natural processes or may be made by synthetic methods.

Modifications include stapling, acetylation, acid addition, acylation, ADP-ribosylation, aldehyde addition, alkylamide addition, amidation, amination, biotinylation, carbamate addition, chloromethyl ketone addition, covalent attachment of a nucleotide or nucleotide derivative, cross-linking, cyclization, disulfide bond formation, demethylation, ester addition, formation of covalent cross-links, formation of cysteine-cysteine disulfide bonds, formation of pyroglutamate, formylation, gamma-carboxylation, glycosylation, GPI anchor formation, hydrazide addition, hydroxyamic acid addition, hydroxylation, iodination, lipid addition, methylation, myristoylation, oxidation, PEGylation, proteolytic processing, phosphorylation, prenylation, palmitoylation, addition of a purification tag, pyroglutamyl addition, racemization, selenoylation, sulfonamide addition, sulfation, transfer-RNA mediated addition of amino acids to proteins such as arginylation, ubiquitination, and urea addition. (see, e.g., Creighton et al. (1993) Proteins—Structure and Molecular Properties, 2nd Ed., T. E. Creighton, W. H. Freeman and Company, New York; Johnson, ed. (1983) Posttranslational Covalent Modification Of Proteins, Academic Press, New York; Seifter et al. (1990) Meth. Enzymol., 182: 626-646; Rattan et al. (1992) Ann. N.Y. Acad. Sci., 663: 48-62; and the like).

Using known methods of protein engineering and recombinant DNA technology, variants may be generated to improve or alter the characteristics of the peptides described herein. Such variants include deletions, insertions, inversions, repeats, duplications, extensions, and substitutions (e.g., conservative substitutions and/or substitutions with nonstandard amino acids) selected according to general rules well known in the art so as have little effect on activity.

Compositions

Also provided herein is a composition comprising any antibacterial peptide described above and a pharmaceutically appropriate excipient, a carrier and/or a drug delivery agent.

In various embodiments, the composition can comprise from about 0.01 to 500 μg/ml, from about 0.01 to 400 μg/ml, from about 0.01 to 300 μg/ml, from about 0.01 to 200 μg/ml, from about 0.01 to 190 μg/ml, from about 0.01 to 180 μg/ml, from about 0.01 to 170 μg/ml, from about 0.01 to 160 μg/ml, from about 0.01 to 150 μg/ml, from about 0.01 to 140 μg/ml, or from about 0.01 to 130 μg/ml of the antibacterial peptide. For example, the composition can comprise from about 0.01 to 128 μg/ml of the antibacterial peptide.

Pharmaceutical compositions containing one or more of the antibacterial peptides described herein can be formulated in any conventional manner. Proper formulation is dependent in part upon the route of administration selected. Routes of administration include, but are not limited to parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, oral, orthotopic, intratracheal, intralesional, percutaneous, endoscopical, transmucosal, sublingual and intestinal administration. Preferably, the composition is administered orally.

The compositions described herein can also comprise one or more pharmaceutically acceptable excipients and/or carriers. The pharmaceutically acceptable excipients and/or carriers for use in the compositions of the present invention can be selected based upon a number of factors including the particular compound used, and its concentration, stability and intended bioavailability; the subject, its age, size and general condition; and the route of administration. The peptides described herein may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces. These biologically active or inert agents can include, for example, enzyme inhibitors and absorption enhancers.

Some examples of materials which can serve as pharmaceutically acceptable carriers in the compositions described herein are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil; and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; artificial cerebral spinal fluid (CSF), and phosphate buffer solutions, as well as other non-toxic compatible lubricants such as sodium lauryl sulfate and magnesium stearate, as well as coloring agents, releasing agents, coating agents, sweetening, flavoring, and perfuming agents, preservatives and antioxidants can also be present in the composition, according to the judgment of the formulator based on the desired route of administration.

The pharmaceutical compositions can be formulated for oral administration. The pharmaceutical compositions can be formulated as tablets, dispersible powders, pills, capsules, gel-caps, granules, solutions, suspensions, emulsions, syrups, elixirs, troches, lozenges, or any other dosage form that can be administered orally. The pharmaceutical compositions can include one or more pharmaceutically acceptable excipients. Suitable excipients for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such solid dosage forms can be uncoated or can be coated to delay disintegration and absorption.

The pharmaceutical compositions can also be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

Additional pharmaceutically acceptable excipients are identified, for example, in The Handbook of Pharmaceutical Excipients, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

In addition, various drug delivery agents may be included in the compositions to facilitate delivery of the peptides to their target. These drug delivery agents can comprise nanoparticles, microparticles, liposomes or others. The peptides can be covalently or non-covalently associated with the delivery vehicles via a linkage that may be suitably cleaved at the target.

In general, the compositions may be formulated to enhance the delivery of the peptides according to standard procedures in the art. Procedures for delivering peptides are described, for example in Bruno et al., (Basics and recent advances in peptide and protein drug delivery, Ther Deliv. 2013; 4(11): 1443-1467) and in Jitendra et al., (Noninvasive Routes of Proteins and Peptides Drug Delivery, Indian J Pharm Sci. 2011; 73(4):367-75). The disclosures of Bruno et al. and Jitendra et al. are incorporated herein by reference in their entirety.

In addition, the composition can further comprise an antibiotic comprising a β-lactam ring. The antibiotic can comprise a penicillin, a carbapanem or a panem. For example, the antibiotic can comprise Benzylpenicillin, Benzathine benzylpenicillin, Procaine benzylpenicillin, Phenoxymethylpenicillin, Propicillin, Pheneticillin, Azidocillin, Clometocillin, Penamecillin, Cloxacillin, Oxacillin, Nafcillin, Methicillin, Amoxicillin, Ampicillin, Epicillin, Ticarcillin, Carbenicillin, Carindacillin, Temocillin, Piperacillin, Azlocillin, Mezlocillin, Mecillinam, Sulbenicillin, Faropenem, Ritipenem, Ertapenem, Antipseudomonal, Biapenem, Panipenem, Cefazolin, Cefalexin, Cefadroxil, Cefapirin, Cefazedone, Cefazaflur, Cefradine, Cefroxadine, Ceftezole, Cefaloglycin, Cefacetrile, Cefalonium, Cefaloridine, Cefalotin, Cefatrizine, Cefixime, Ceftriaxone, Cefotaxime, Cefdinir, Cefcapene, Cefdaloxime, Ceftizoxime, Cefmenoxime, Cefpiramide, Cefpodoxime, Ceftibuten, Cefditoren, Cefotiam, Cefetamet, Cefodizime, Cefpimizole, Cefsulodin, Cefteram, Ceftiolene, Oxacephem, Cefepime, Cefozopran, Cefpirome, Cefquinome, Ceftaroline fosamil, Ceftolozane, Ceftobiprole, Ceftiofur, Cefquinome, Cefovecin, Aztreonam, Tigemonam, Carumonam, and Nocardicin A, Doribax, Invanz, Merrem IV, Imipenem/Cilastatin, Meropenem/Vaborbactam, Imipenem/Cilastatin/Relebactam, Primaxin, Recarbrio, Vabomere, Imipenem, Panipenem/betamipron, Tebipenem, Ertapenem, Doripenem, Meropenem, Faropenem, Ritipenem, a prodrug thereof, or any combination thereof. Preferably, the antibiotic comprises a penicillin or a carbapenem. For example, the antibiotic can comprise amoxicillin or a carbapenem.

Methods of Decreasing Bacterial Titer and/or Treating Bacterial Infection

Also provided are methods of reducing a bacterial titer. Also provided are medicaments comprising the peptides or compositions described above in the use of reducing a bacterial titer.

The method of reducing a bacterial titer can comprise applying any of the antibacterial peptides or compositions comprising the antibacterial peptides as described above to the bacteria. In various embodiments, the bacteria are located within a subject (i.e., an animal, plant, or other organism). Accordingly, the method may further comprise administering the antibacterial peptide or composition comprising the antibacterial peptide to the subject. In various embodiments, the peptides comprise a CPP to enhance damage to the bacterial cell membrane.

In various embodiments, the method may further comprise applying an antibiotic to the bacteria, or administering an antibiotic to the subject. The antibiotic preferably comprises a β-lactam ring. Adding β-lactam with the peptide can significantly enhance bactericidal effect compared to peptide alone. For example, the antibiotic can comprise any antibiotic described herein above. In various embodiments, the method may comprise applying or administering another β-lactamase inhibitor drug to the bacteria or subject, either in combination with an antibiotic or without an antibiotic. The antibiotic and additional β-lactamase inhibitor drug can independently be applied or administered in the same composition as the antibacterial peptides or in one or more separate compositions, which may be applied or administered simultaneously or sequentially.

The target bacteria may show resistance to the antibiotic. That is, it may show less sensitivity to the antibiotic's effect on its growth rate, replication rate, virulence, or other some other measure known in the art as compared to a bacterium that has not developed resistance to the antibiotic. One way to measure the bacteria's sensitivity can be to measure the minimum inhibitor concentration (MIC) of the antibiotic against the bacteria according to Clinical and Laboratory Standards Institute protocols. For example, one protocol is described in the following document: CLSI. *Methods for Dilution Antimicrobial Susceptibility Tests for Bacteria That Grown Aerobically; Approved Standard—Tenth Edition*. CLSI document M07-A10, Wayne Pa.: Clinical and Laboratory Standards Institute, 2015, incorporated herein by reference in its entirety. The antibacterial peptide may increase sensitivity (decrease resistance) to the antibiotic. For example, the antibacterial peptide can decrease the minimum inhibitory concentration (MIC) of the antibiotic against the bacteria as compared to the MIC of the antibiotic without the antibacterial peptide.

The bacteria can express a β-lactamase and the antibacterial peptide can inhibit the ability of the β-lactamase to cleave a β-lactam ring. This can be measured using a beta lactamase inhibition assay like a commercially available beta lactamase inhibitor screening kit. These kits test the ability of a beta lactamase to hydrolyze a chromogenic substrate, which results in the generation of a colored product. The amount of color produced is directly proportional to the amount of beta-lactamase activity. In the presence of beta lactamase inhibitors, such as clavulanic acid or the antibacterial peptides described herein, the rate of substrate hydrolysis will decrease resulting in a decrease in the production of colored analyte. In various embodiments, the antibacterial peptide inhibits β-lactamase equally well or better than a non-peptide β-lactamase inhibitor and/or is more tolerant to bacterial mutations. The non-peptide β-lactamase inhibitor can comprise clavulanate, clavulanic acid, sulbactam, taobactam, avibactam, relebacam, RG6080, or RPX7009.

The bacteria can comprise any gram negative or gram positive bacteria described herein above. For example, the bacteria can comprise *Escherichia coli* ATCC 35218 or *Staphylococcus aureus.*

In various embodiments, the methods can further comprise treating a bacterial infection in a subject in need thereof. The method of treating a bacterial infection can comprise administering an effective amount of the antibacterial peptide or compositions comprising the antibacterial peptide to the subject, as described above. The method may further comprise administering an antibiotic, another β-lactamase inhibitor drugs, or combinations thereof to the subject, as described above. The subject can be an animal or a plant. In some embodiments, the subject is an animal (i.e., a human).

The bacterial infection can be caused by any gram negative or gram positive bacteria described above. For example, the bacteria can comprise *Escherichia coli, Acinetobacter baumannii, Neisseria gonorrhoeae, Moraxella catarrhalis, Shigella, Klebsiella, Enterobacter aerogenes, Enterobacter cloacae, Proteus, Mycolicibacterium fortuitum* (*Mycobacterium fortuitum*), *Mycobacterium tuberculosis, Aeromonas hydrophila, Pseudomonas aeruginosa, Stenotrophomonas maltophilia* (*Pseudomonas maltophilia*), *Rhodobacter capsulatus* (*Rhodopseudomonas capsulata*), *Haemophilus influenzae, Vibrio cholerae, Citrobacter, Yersinia, Serratia, Salmonella, Kluyvera, Staphylococcus aureus, Streptococcus pneumoniae, Bacillus subtilis, Bacillus licheniformis, Bacillus cereus, Bacillus amyloliquefaciens* (*Bacillus velezensis*), *Bacillus thuringiensis, Bacillus mycoides, Streptomyces cellulosae, Streptomyces badius, Streptomyces cacaoi, Streptomyces fradiae* (*Streptomyces roseoflavus*), *Kitasatospora aureofaciens* (*Streptomyces aureofaciens*), *Streptomyces albus* G, *Streptomyces lavendulae, Nocardia, Amycolatopsis, Mycolicibacterium fortuitum* (*Mycobacterium fortuitum*), *Mycobacterium tuberculosis*, or any combination thereof.

When the infection occurs in an animal system (e.g., when the subject is an animal), it can occur in any organ system, including but not limited to, the digestive system, the cardiovascular system, the respiratory system, or the reproductive system.

The effective amount of the antibacterial peptide can depend on whether the peptide is administered in vivo (i.e., in a subject to treat a bacterial infection) or in vitro (i.e., to reduce bacterial titer in a dish). In vitro, an effective amount of the antibacterial peptide can comprise from about 0.01 to 500 μg/ml, from about 0.01 to 400 μg/ml, from about 0.01 to 300 μg/ml, from about 0.01 to 200 μg/ml, from about 0.01 to 190 μg/ml, from about 0.01 to 180 μg/ml, from about 0.01 to 170 μg/ml, from about 0.01 to 160 μg/ml, from about 0.01 to 150 μg/ml, from about 0.01 to 140 μg/ml, or from about 0.01 to 130 μg/ml of the antibacterial peptide. For example, the effective amount can comprise from about 0.01 to 128 μg/ml of the antibacterial peptide. In vivo, the effective amount of the antibacterial peptide can comprise from about 0.01 to 1000 mg/kg, from about 0.01 to 900 mg/kg, from about 0.01 to 800 mg/kg, from about 0.01 to 700 mg/kg, from about 0.01 to 600 mg/kg, or from about 0.01 to 500 mg/kg. For example, the effective amount of the antibacterial peptide can comprise from about 0.01 to 500 mg/kg.

The method can further comprise administering an antibiotic to the subject. The antibiotic can comprise any antibiotic described herein above (i.e., comprises a β-lactam ring). The method can cover any method or sequence of administration of the antibiotic and the antibacterial peptide. For example, the antibiotic and antibacterial peptide can be administered separately or together. The antibiotic can be administered before the peptide or vice-versa.

EXAMPLES

The following non-limiting examples are provided to further illustrate the present invention.

Example A: Method of Making TEM-1 Inhibitory Peptides

TEM-1 inhibitory peptides were synthesized according to previously published methods for standard solid phase chemical synthesis (Merrifield, R. B. "Solid Phase Peptide Synthesis I. The Synthesis of a Tetrapeptide." (1963) Journal of the American Chemical Society, 85, 2149-2154).

Example 1: In Vitro TEM-1 Inhibitory Peptide Screening $K_i$ of the peptide inhibitors were measured using the standard β-lactamase inhibitor screening assay. Briefly, the peptides at various concentrations were pre-incubated with 10 nM TEM-1 at room temperature for 10 minutes prior loading to a 96-well plate. Nitrocefin was then added to the mixture to reach a final concentration of 20 μM, and the OD486 nm was continuously recorded for the first 1 minutes. The reaction rate, $IC_{50}$ (not shown) and $K_i$ (Table 5) were then calculated. The $K_i$ for the M69L TEM-1 mutant was determined at 100 nM enzyme concentration because of its slowed enzyme kinetics. The $K_i$ of clavulanate was measured by mixing with enzyme and nitrocefin at the same time because it covalently modifies the enzyme.

TABLE 5

Ki of lead peptides in inhibiting TEM-1 and TEM-1 M69L mutant.

| Inhibitor | TEM-1 Ki (μM) | M69L Ki(μM) | Sequence (SEQ ID NO:) | Binding motif** (SEQ ID NO:) |
|---|---|---|---|---|
| T61-25 | 1.79 | 25.7 | KTYLAQAAATG (SEQ ID NO: 5) | (K/R/H)x(Y/F)(L/I/V)xx(A/V/L/I/)Axxx (SEQ ID NO: 1) |
| T63-04 | 0.13 | 17.2 | HSGVASAAAG (SEQ ID NO: 6) | (H/K/R)xx(V/I/L)xx(A/L/I/V)Axx (SEQ ID NO: 2) |
| T63-07 | 2.76 | 18.2 | KTFVVRALAS (SEQ ID NO: 7) | (K/R/H)(T/S)xx(V/L/I)xx(L/I/V/A)Ax (SEQ ID NO: 3) |
| T66-12 | 0.16 | 14.1 | GGSGDFARSSY (SEQ ID NO: 8) | xxxx(D/E)(F/Y)x(R/K/H)Sxx (SEQ ID NO: 4) |
| RRGHYY-NH2* | 136 | — | | |
| Clavulanate | 1.9 | 47 | | |

*Wanzhi Huang, Zanna Beharry, Zhen Zhang and Timopthy Palzkill. (2003) A broad-spectrum peptide inhibitor of β-lactamase identified using phase display and peptide arrays. Protein Engineering. Vol. 16 no. 11, pp 853-860

**Two different binding modes were observed as for the four peptides. Specifically, T61-25, T63-04, and T63-07 share a similar binding mode. T66-12 presents a distinct binding mode. Critical residues (motif) of each peptide for binding are shown in Table 5.

Example 2: In Vivo Antimicrobial Susceptibility Test

The activity of peptide inhibitors was assessed in *Escherichia coli* ATCC 35218 strain, which is a TEM-1 producing control *E. coli* strain commonly used in testing β-lactamase inhibitor activity, and which is resistant to amoxicillin by expressing TEM-1 β-lactamase. Peptide inhibitors that can inhibit TEM-1 function will lower minimum inhibitory concentration (MIC) of the amoxicillin against the resistant bacteria, which will be used to measure the potency of peptide inhibitors in bacteria. Bacterial susceptibility to amoxicillin and β-lactamase inhibitors were determined by broth microtiter dilution (BMD) according to the Clinical and Laboratory Standards Institute (CLSI) methodology. The tests were done using checkboard method with different amoxicillin concentrations (0-128 μg/ml). For the control group, clavulanic acid concentration was about 4 μg/ml.

None of the peptides without CPP enhanced amoxicillin potency against ATCC35218 (data not shown) likely because *E. coli* cannot take up peptides larger than 6 aa. Peptide uptake was enhanced by attaching two different cell wall-permeating peptides (CPP) to peptide T61-025 to form T63-1 (KFFKFFKFFKKTYLAQAAATG, SEQ ID NO: 64) and T63-2 (CFFKDELKTYLAQAAATG, SEQ ID NO: 65)(FIG. 1). Significant enhancement of amoxicillin killing of bacteria was observed with T63-1 while T63-2 demonstrated moderate effect at enhancing amoxicillin potency (FIG. 1). In addition, T63-1 enhanced amoxicillin potency significantly more than clavulanate.

Figure 2A:
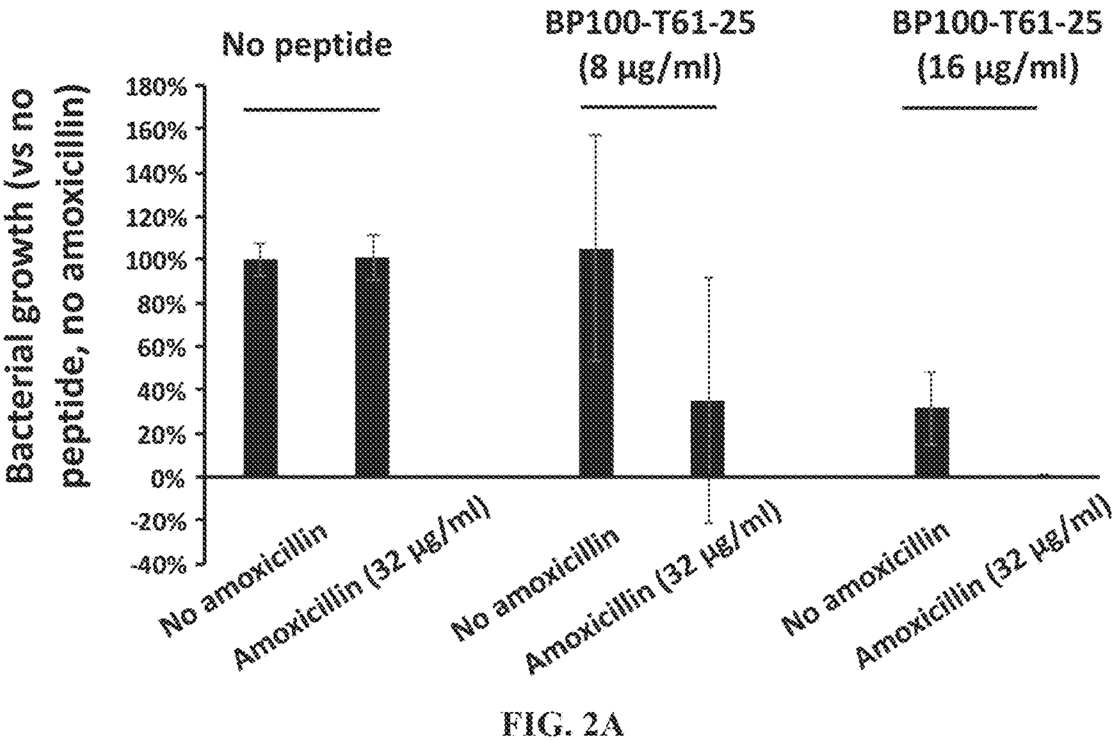
FIG. 2A shows the growth of ATCC35218 treated with 32 μg/ml amoxicillin with peptides BP100-T61-25 at different concentrations.

In order to further improve the potency of the peptides, peptide T61-25 (KTYLAQAAATG) was attached to BP100 (KKLFKKILKYL)(SEQ. ID. NO. 11) to form BP100-T61-25 (KKLFKKILKYLKTYLAQAAATG, SEQ ID NO: 66) and tested in ATCC35218 (FIG. 2A). Marked enhancement of amoxicillin (32 μg/ml) killing of bacteria was observed (FIG. 2A). BP100-T61-25 with 32 μg/ml amoxicillin demonstrated strong inhibition of bacterial growth at 8-16 μg/ml, though it also significantly inhibited bacterial growth without amoxicillin at 16 μg/ml, suggesting the CPP may be toxic to the bacteria at this concentration and can damage the *E. coli* bacterial cell wall by itself. Nevertheless, at 8 μg/ml, BP100-T61-25 with amoxicillin significantly enhanced amoxicillin killing of *E. coli*. The large variation among samples at 8 μg/ml BP100-T61-25 treatment with amoxicillin was caused by one bacterial sample growing while other samples failed to grow, suggesting the dose was close to the MIC.

Figure 2B:
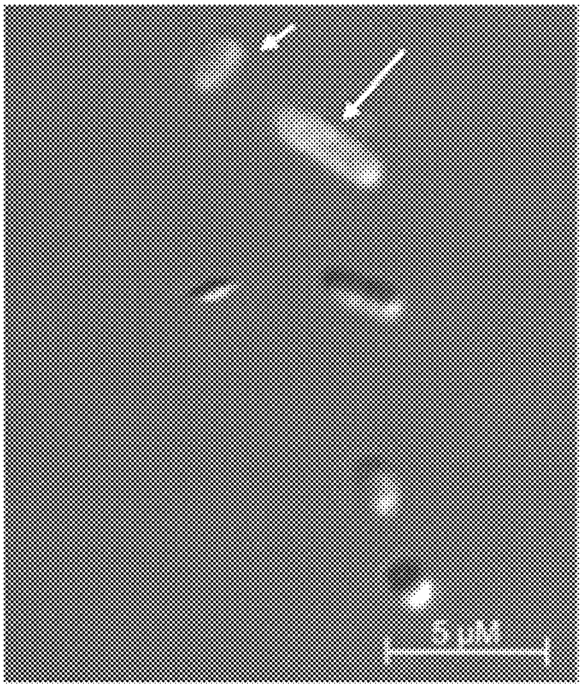
FIG. 2B shows confocal microscopy images of ATCC35218 upon treatment with fluorescent labeled BP100-T61-25. Arrows indicate cells exhibiting green fluorescence if BP100-T61-25 peptides successfully cross bacterial membranes in overlay image of brightfield and fluorescence field.
Figure 2C:
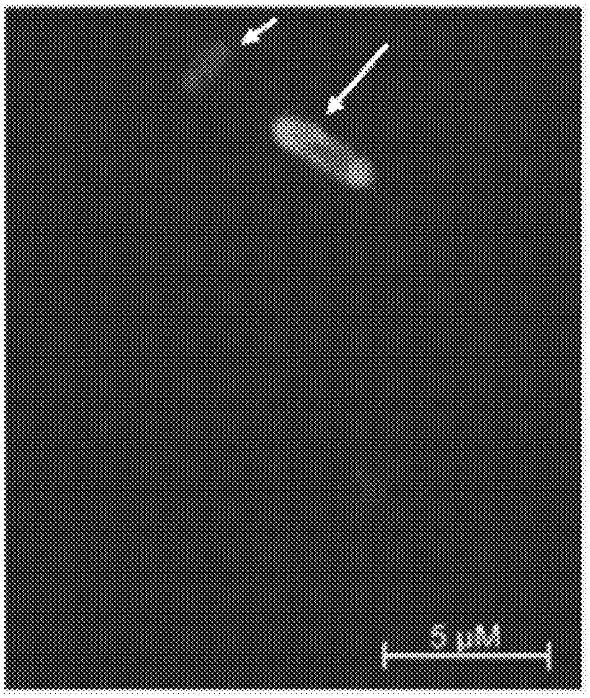
FIG. 2C show confocal microscopy images of ATCC35218 upon treatment with fluorescent labeled BP100-T61-25. Arrows indicate cells exhibiting green fluorescence if BP100-T61-25 peptides successfully cross bacterial membranes in image of fluorescence field.

To confirm that the CPP enhanced the *E. coli* uptake of the peptide, the BP100-T61-25 peptide was labeled with 5(6)-FAM [5-(and-6)-Carboxyfluorescein at the N-terminus and incubated with ATCC35218 cells. The peptide localization was visualized by confocal microscopy, and peptide internalization into *E. coli* cells was observed (FIG. 2B), verifying that the CPP enhanced peptide uptake. It is noted that significant enhancement of amoxicillin potency against resistant bacteria can be achieved by linking CPPs to peptide inhibitor.

Example 3: In Vivo Antimicrobial Susceptibility Test for Gram Positive Bacteria *Staphylococcus aureus*

More than 90% of staphylococcal isolates now produce penicillinase. Staphylococcal resistance to penicillin is mediated by blaZ, the gene that encodes β-lactamase, which sharing significant homology with the TEM-1 coding gene. As a result, it is predicted that the peptide inhibitors designed against TEM-1 will also inhibit penicillinase in *S. aureus*. We thus tested the peptide's potency at enhancing amoxicillin killing a Methicillin-resistant *Staphylococcus aureus* (MRSA) stain NRS384.

MRSA is approaching an epidemic level and is categorized as a serious threat by the CDC. In addition to β-lactamase, MRSA contains the mecA gene in a mobile genetic element found in all MRSA strains, which encodes penicillin-binding protein 2a (PBP2a). PBPs are membrane-bound enzymes that catalyze the transpeptidation reaction that is necessary for cross-linkage of peptidoglycan chains for cell wall formation, and is targeted by β-lactam. Because of the low affinity of PBP2a for β-lactam antibiotics, it can substitute for other PBPs under high concentrations of β-lactam antibiotics. As a result, MRSA strains are highly resistant to β-lactam antibiotics.

Figure 3A:
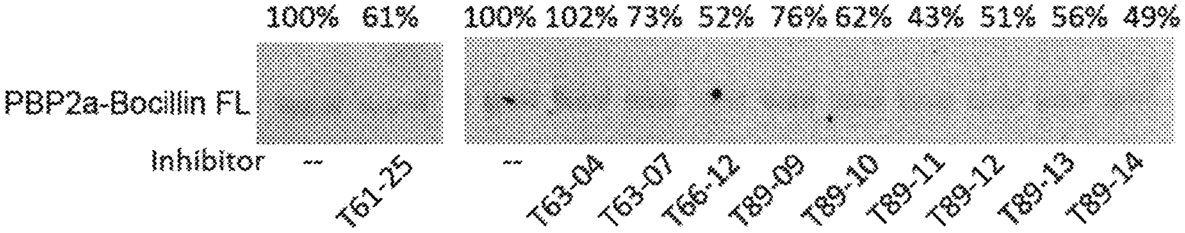
FIG. 3A shows peptides inhibited PBP2a binding to substrate Bocillin FL.

More peptides were designed to target both PBP2a and β-lactamase which are predicted to enhance amoxicillin killing of MRSA. Peptides designed by an in silico screening method successfully inhibited penicillin binding to PBP2a and enhanced bacteria killing by amoxicillin. The top 6 best-scored peptides were synthesized. An in vitro binding assay was carried out on these peptides and 4 known β-lactamase inhibitor peptides, T61-25, T63-04, T63-07, T66-12 (FIG. 3A) by incubating the candidate peptides with PBP2a (RayBiotech, GA) in the presence of Bocillin FL, a fluorescent penicillin. In the absence of peptide competitors, Bocillin FL bound to PBP2a and then gave rise to fluorescence signal when the protein was resolved on an SDS-PAGE gel. Preliminary data show that 6 peptides inhibited Bocillin FL binding to PBP2a (FIG. 3A). Encouragingly, T61-25, T63-07 and T66-12 demonstrated an inhibitory effect on both β-lactamase and PBP2a (Table 5 and FIG. 3A). T61-25 was chosen as a lead candidate targeting both β-lactamase and PBP2a.

Figure 3B:
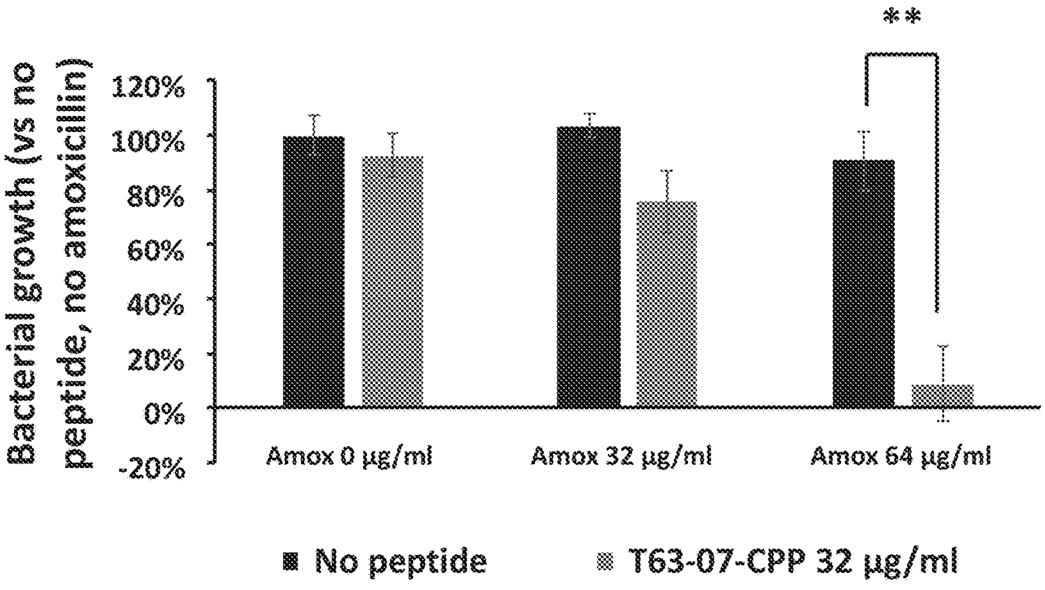
FIG. 3B shows growth of NRS384 treated with 32 μg/ml peptide T63-07-CPP at different concentrations of amoxicillin (*p<0.05, **p<0.01).

In order to assess the potency of the peptides against MRSA, the peptides were tested on MRSA strain NRS384, which is widely used for studying MRSA infections. Peptide inhibitors that can inhibit penicillinase and/or PBP2a function will lower the minimum inhibitory concentration (MIC) of amoxicillin against the resistant bacteria. The peptide-CPP's potency at enhancing amoxicillin killing of NRS384 (MIC for amoxicillin>256 μg/ml) was tested. Peptide T63-07-CPP ((T63-07 (KTFVVRALAS)(SEQ ID NO: 7) conjugated with CPP KFFKFFKFFK (SEQ ID NO: 9) to form KTFVVRALASCKFFKFFKFF, SEQ ID NO: 67) at 32 μg/ml was able to significantly enhance the amoxicillin (32 and 64 μg/ml) inhibition of MRSA growth, suggesting the peptide can markedly inhibit the β-lactam resistance in the MRSA that is mediated by both penicillinase and PBP2a (FIG. 3B). Peptide BP100-T61-25 (KKLFKKILKYLKTYLAQAAATG) was also able to enhance the killing of amoxicillin (32 μg/ml) of MRSA at a lower concentration (16 μg/ml) (FIG. 3C), demonstrating better potency than CPP-T63-07. It is highly encouraging that not only can the peptide inhibitors reduce MRSA resistance to β-lactam, but also can completely inhibit MRSA growth in combination with amoxicillin, indicating they inhibited both penicillinase and PBP2a. These data support the structure analysis that PBP2a shares structural similarity with β-lactamases in the penicillin-binding domain, and that peptides can inhibit both proteins to achieve greater inhibition of (3-lactam resistance in MRSA.

Some of the MRSA strains also developed resistance against cephalosporin, which are improved β-lactams developed to overcome some of the early penicillin resistance.

Figure 4:
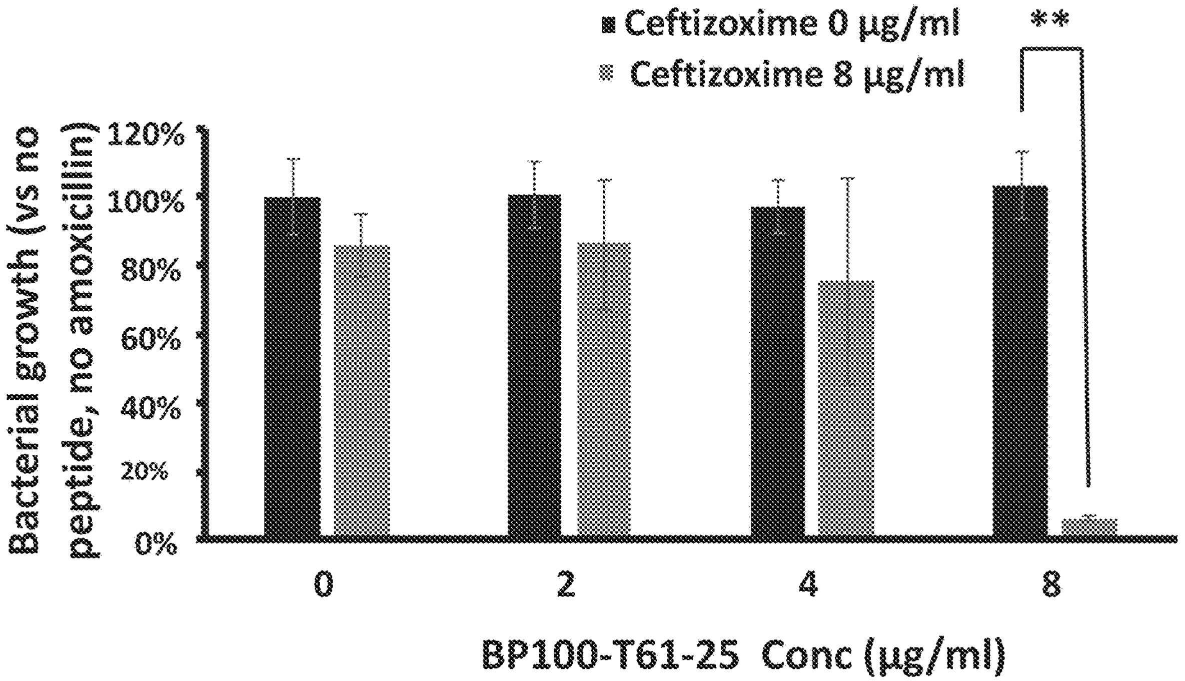
FIG. 4 shows growth of MRSA bacteria when treated with BP100-T61-25 at different concentration with no or 8 μg/ml ceftizoxime (*p<0.05, **p<0.01).

BP100-T61-25's synergy with Ceftizoxime, which is a third generation cephalosporin on a MRSA strain (JE2) that is resistant to cephalosporin, was tested. BP100-T61-25 at 8 μg/ml can significantly enhance ceftizoxime's killing of JE2 (FIG. 4).

Figure 3C:
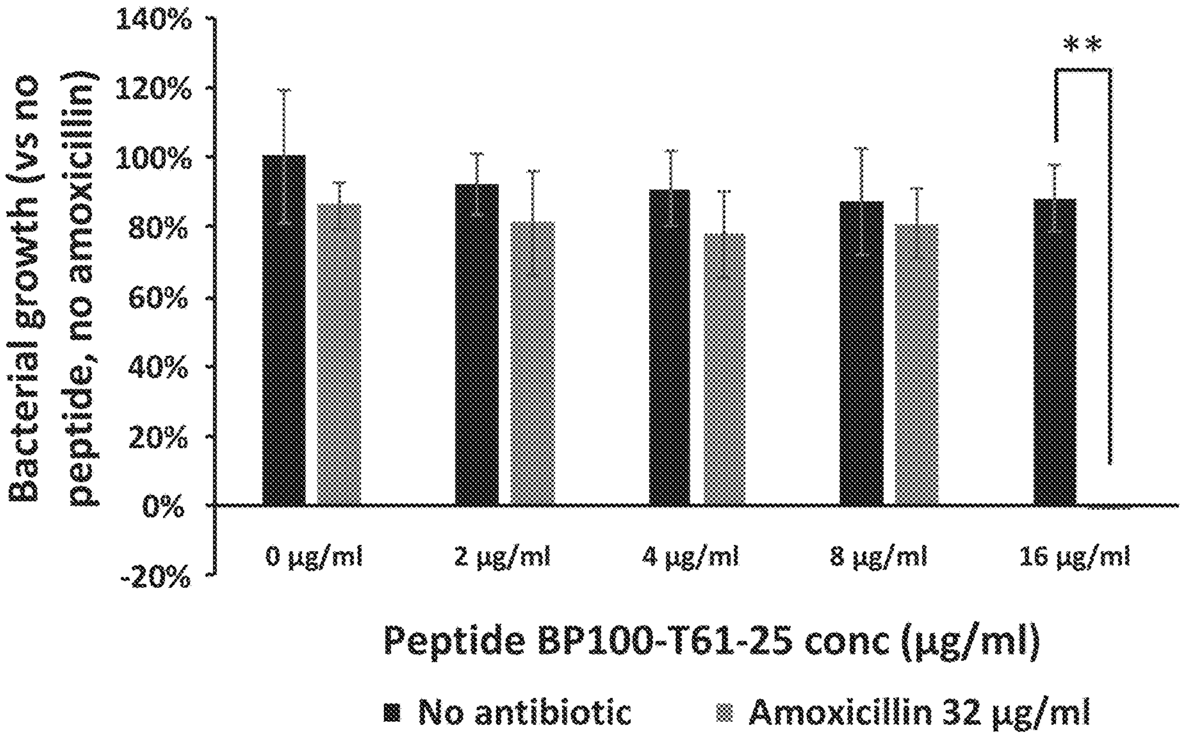
FIG. 3C shows growth of NRS384 treated with BP100-T61-25 at different concentration with 32 μg/ml amoxicillin (*p<0.05, **p<0.01)).
Figure 5A:
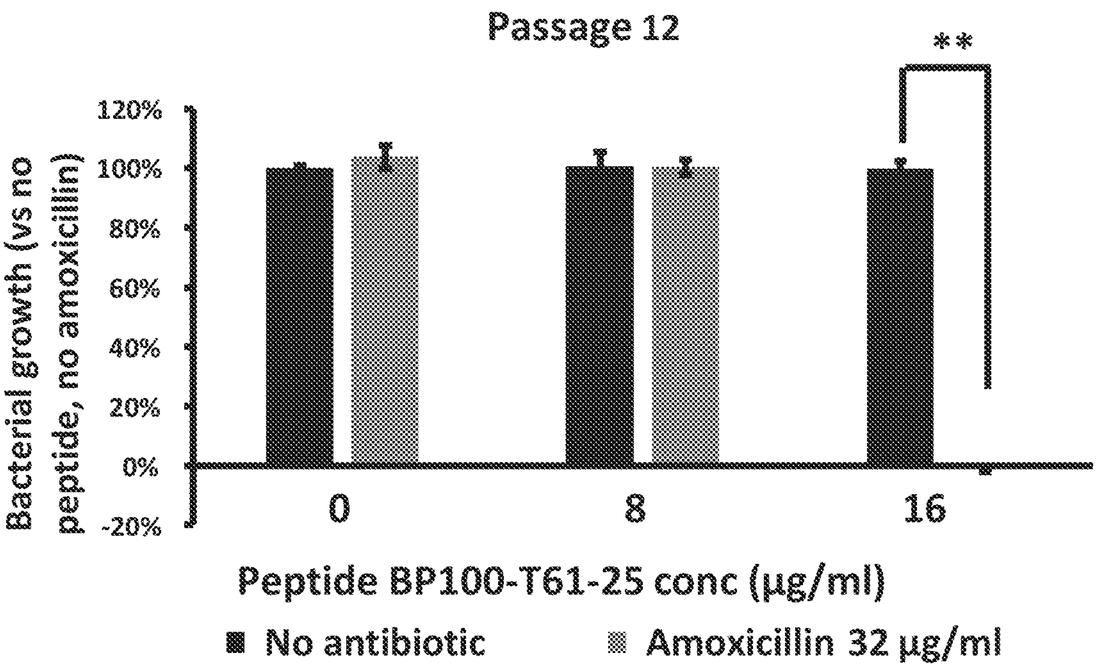
FIGS. 5A, 5B, 5C and 5D show growth of bacteria selected after different passages with BP100-T61-25 and amoxicillin, treated with 32 μg/ml amoxicillin with BP100-T61-25 at different concentrations (*p<0.05, **p<0.01).
Figure 5B:
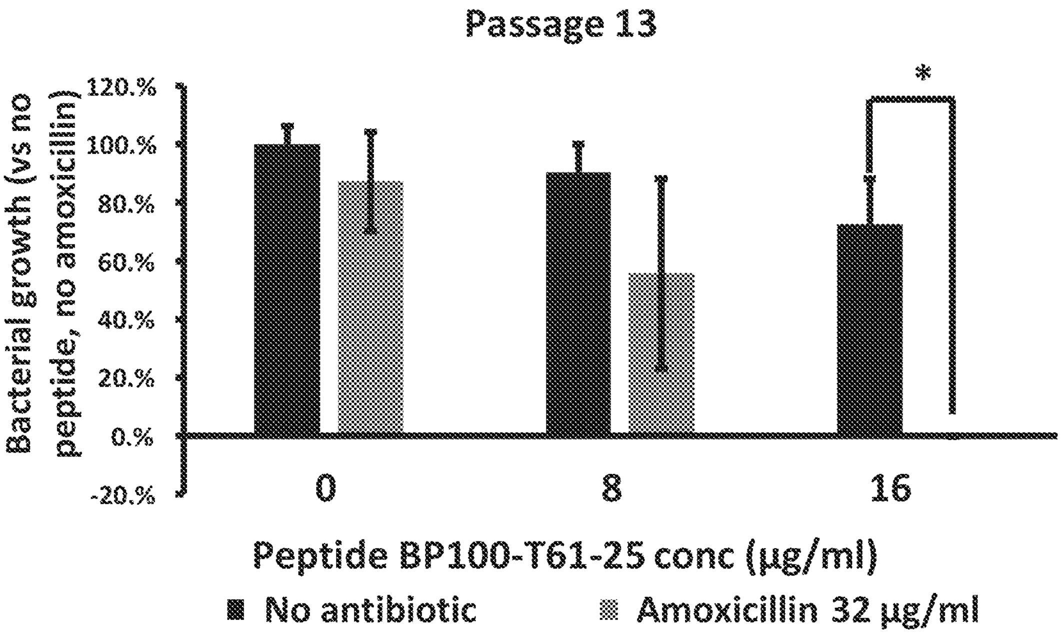
Figure 5C:
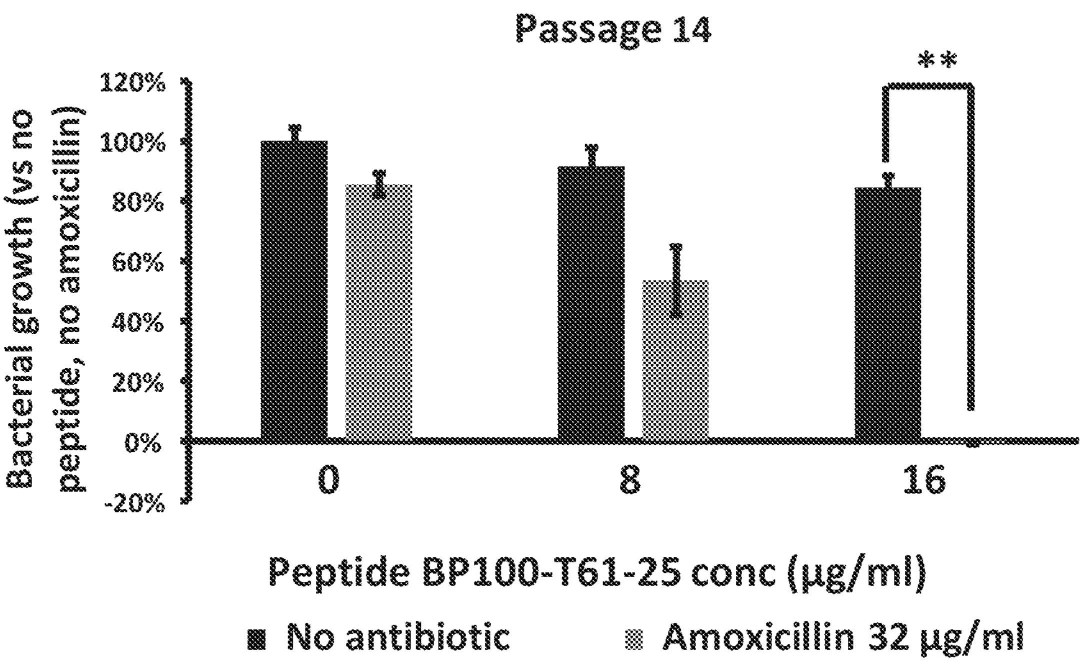
Figure 5D:
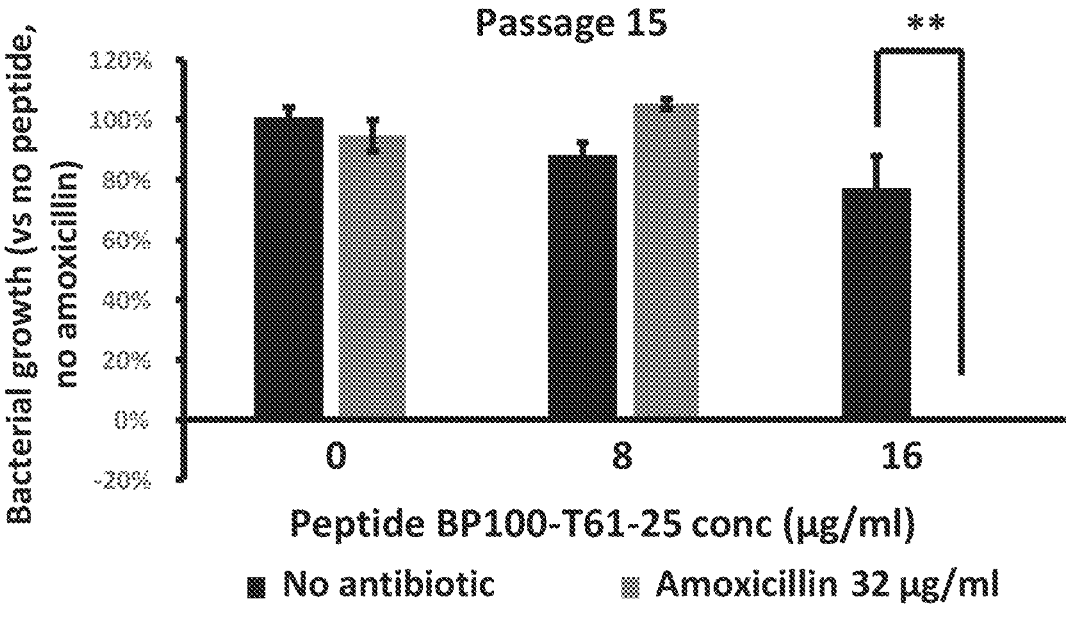
Figure 5E:
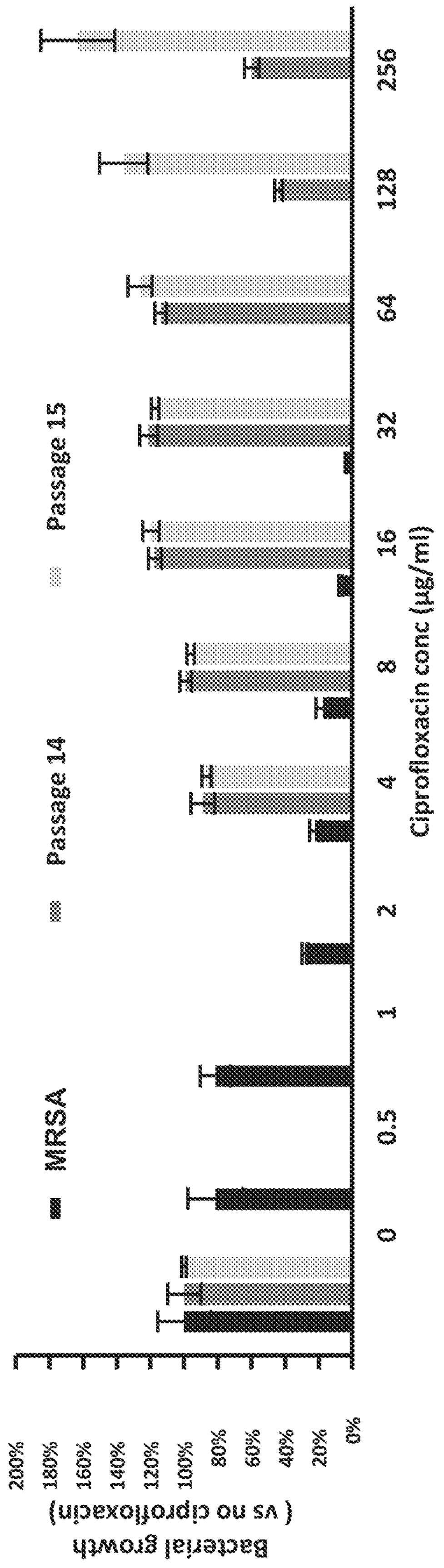
FIG. 5E shows growth of bacteria selected by ciprofloxacin after different passage treated with ciprofloxacin at different concentrations (*p<0.05, **p<0.01).

MRSA is less likely to develop resistance to peptide inhibitors than conventional antibiotics: NRS384 was subjected to serial passage in the presence of ½ MIC of peptide/32 μg/ml amoxicillin for 15 passages and ciprofloxacin was used as control for resistance selection, following a protocol for studying antimicrobial peptide resistance. Encouragingly, 16 μg/ml BP100-T61-25 peptide/32 μg/ml amoxicillin was sufficient to inhibit bacterial growth in passages 12-15 (FIGS. 5A, 5B, 5C and 5D), as efficient as in the original NRS384 strain (FIG. 3C). On the other hand, bacterial MIC to ciprofloxacin at passages 14-15 has risen to >256 μg/ml (FIG. 5E). The preliminary result suggests that there is a markedly reduced tendency of MRSA to develop resistance to peptide inhibitors as compared to conventional antibiotics such as ciprofloxacin.

REFERENCES

1. CDC, ANTIBIOTIC RESISTANCE THREATS IN THE UNITED STATES, 2019, (2019).
2. U. Hofer, The cost of antimicrobial resistance, Nature reviews. Microbiology 17(1) (2019) 3.
3. K. Tehrani, N. I. Martin, beta-lactam/beta-lactamase inhibitor combinations: an update, Medchemcomm 9(9) (2018) 1439-1456.
4. J. D. Docquier, S. Mangani, An update on beta-lactamase inhibitor discovery and development, Drug Resist Updat 36 (2018) 13-29.
5. O. N. Silva, O. L. Franco, W. F. Porto, beta-Lactamase inhibitor peptides as the new strategies to overcome bacterial resistance, Drugs Today (Barc) 54(12) (2018) 737-746.
6. J. L. Lau, M. K. Dunn, Therapeutic peptides: Historical perspectives, current development trends, and future directions, Bioorg Med Chem 26(10) (2018) 2700-2707.
7. W. Huang, Z. Beharry, Z. Zhang, T. Palzkill1, A broad-spectrum peptide inhibitor of b-lactamase identified using phage display and peptide arrays, Protein Engineering 16(11) (2003) 853-860.
8. CLSI, Methods for Dilution Antimicrobial Susceptibility Tests for Bacteria That Grow Aerobically; Approved Standard—Tenth Edition, Clinical and Laboratory Standards Institute, Wayne, PA 19087 USA, 2015.
9. F. D. Lowy, Antimicrobial resistance: the example of *Staphylococcus aureus*, J. Clin. Invest 111(9) (2003) 1265-1273.
10. Oikawa et al., Screening of a Cell-Penetrating Peptide Library in *Escherichia coli*: Relationship between Cell Penetration Efficiency and Cytotoxicity. ACS Omega 2018, 3, 16489-164.
11. Walker, J. R. & Altman, E. Biotinylation facilitates the uptake of large peptides by *Escherichia coli* and other gram-negative bacteria. *Applied and environmental microbiology* 71, 1850-1855 (2005).
12. Good, L., Awasthi, S. K., Dryselius, R., Larsson, O. & Nielsen, P. E. Bactericidal antisense effects of peptide-PNA conjugates. *Nature biotechnology* 19, 360-364 (2001).
13. Rajarao, G. K., Nekhotiaeva, N. & Good, L. Peptide-mediated delivery of green fluorescent protein into yeasts and bacteria. *FEMS Microbiol Lett* 215, 267-272 (2002).
14. Rodloff, A., Bauer, T., Ewig, S., Kujath, P. & Müller, E. Susceptible, intermediate, and resistant—the intensity of antibiotic action. *Deutsches Arzteblatt international* 105, 657-662 (2008).
15. Pérez-Peinado, C. et al. Mechanisms of bacterial membrane permeabilization by crotalicidin (Ctn) and its fragment Ctn (15-34), antimicrobial peptides from rattlesnake venom. *J Biol Chem* 293, 1536-1549 (2018).
16. Lowy, F. D. Antimicrobial resistance: the example of *Staphylococcus aureus. J. Clin. Invest* 111, 1265-1273 (2003).
17. Pinho, M. G., de Lencastre, H. & Tomasz, A. An acquired and a native penicillin-binding protein cooperate in building the cell wall of drug-resistant staphylococci. *Proc Natl Acad Sci USA* 98, 10886-10891 (2001).

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

Having described the invention in detail, it will be apparent that modifications and variations are possible without departing from the scope of the invention defined in the appended claims.

The invention claimed is:

1. An antibacterial peptide comprising a binding motif comprising an amino acid sequence selected from the group consisting of SEQ ID NO:5, SEQ ID NO: 6, SEQ ID NO:7, and SEQ ID NO:8; and a cell wall permeating peptide selected from any one of SEQ ID NOs: 9-63; wherein the antibacterial peptide selectively inhibits β-lactamase.

2. A composition comprising the peptide claim 1 and a pharmaceutically acceptable excipient, carrier and/or drug delivery agent.

3. The composition of claim 2, wherein the composition comprises from about 0.01 to about 128 μg/ml of the peptide.

4. The composition of claim 2, further comprising an antibiotic comprising a β-lactam ring.

5. A method of reducing a titer of bacteria, the method comprising applying an effective amount of the antibacterial peptide of claim 1.

6. The method of claim 5, wherein the bacteria are present in a subject and the method comprises administering the antibacterial peptide to the subject.

7. The method of claim 6, wherein the method further comprises administering the antibiotic to the subject.

8. The method of claim 7, wherein the antibiotic comprises a β-lactam ring.

9. The method of claim 5 further comprising treating a bacterial infection in the subject.

10. The method of claim 9, wherein the bacterial infection is caused by bacteria selected from the group consisting of *Escherichia coli, Acinetobacter baumannii, Neisseria gonorrhoeae, Moraxella catarrhalis, Shigella, Klebsiella, Enterobacter cloacae, Enterobacter aerogenes Proteus, Mycolicibacterium fortuitum* (*Mycobacterium fortuitum*), *Mycobacterium tuberculosis, Aeromonas hydrophila, Pseudomonas aeruginosa, Stenotrophomonas maltophilia* (*Pseudomonas maltophilia*), *Rhodobacter capsulatus* (*Rhodopseudomonas capsulata*), *Haemophilus influenzae, Vibrio cholerae, Citrobacter, Yersinia, Serratia, Salmonella, Kluyvera, Staphylococcus aureus, Streptococcus pneumoniae, Bacillus subtilis, Bacillus licheniformis, Bacillus cereus, Bacillus amyloliquefaciens* (*Bacillus velezensis*), *Bacillus thuringiensis, Bacillus mycoides, Streptomyces cellulosae, Streptomyces badius, Streptomyces cacaoi, Streptomyces fradiae* (*Streptomyces roseoflavus*), *Kitasatospora aureofaciens* (*Streptomyces aureofaciens*), *Streptomyces albus* G, *Streptomyces lavendulae, Nocardia, Amycolatopsis, Mycolicibacterium fortuitum* (*Mycobacterium fortuitum*), *Mycobacterium tuberculosis*, or any combination thereof.

* * * * *